(12) United States Patent
Khan et al.

(10) Patent No.: US 11,726,026 B2
(45) Date of Patent: Aug. 15, 2023

(54) FLUORESCENCE BASED EXTRACELLULAR ENZYME ACTIVITY ASSAY FOR EARLY DETECTION OF BIOFOULING IN SEAWATER DESALINATION SYSTEMS

(71) Applicant: KING ABDULLAH UNIVERSITY OF SCIENCE AND TECHNOLOGY, Thuwal (SA)

(72) Inventors: Babar Khalid Khan, Kingston, NY (US); TorOve Leiknes, Richfield, MN (US)

(73) Assignee: KING ABDULLAH UNIVERSITY OF SCIENCE AND TECHNOLOGY, Thuwal (SA)

(*) Notice: Subject to any disclaimer, the term of this patent is extended or adjusted under 35 U.S.C. 154(b) by 852 days.

(21) Appl. No.: 16/476,444

(22) PCT Filed: Aug. 21, 2017

(86) PCT No.: PCT/IB2017/055042
§ 371 (c)(1),
(2) Date: Jul. 8, 2019

(87) PCT Pub. No.: WO2018/142195
PCT Pub. Date: Aug. 9, 2018

(65) Prior Publication Data
US 2020/0056982 A1    Feb. 20, 2020

Related U.S. Application Data

(60) Provisional application No. 62/453,708, filed on Feb. 2, 2017.

(51) Int. Cl.
*G01N 17/00* (2006.01)
*C12Q 1/34* (2006.01)
*B01D 65/08* (2006.01)

(52) U.S. Cl.
CPC ............ *G01N 17/008* (2013.01); *B01D 65/08* (2013.01); *C12Q 1/34* (2013.01); *C12Q 2334/22* (2013.01)

(58) Field of Classification Search
CPC ...... B01D 65/08; C12Q 2334/22; C12Q 1/34; G01N 17/008
(Continued)

(56) References Cited
U.S. PATENT DOCUMENTS 6,017,459 A    1/2000   Zeiher et al.
6,372,895 B1*  4/2002   Bentsen ............... C07H 17/075
                                                  549/402
(Continued)

FOREIGN PATENT DOCUMENTS

JP    2015199020 A    11/2015
WO   2004009497 A2    1/2004

OTHER PUBLICATIONS

Substantive Examination Report in corresponding/related SA Application No. 519402343, dated Dec. 26, 2021.
(Continued)

*Primary Examiner* — David Z Huang
*Assistant Examiner* — Jean F Morello
(74) *Attorney, Agent, or Firm* — Patent Portfolio Builders PLLC

(57) ABSTRACT

A method and system for early detection of biofouling utilizing a fluorescence based extracellular enzyme activity assay is disclosed. The method provides a means for early detection of biofouling on membranes used in flow-through membrane filtration systems for with a feed water flow, such as waste water of water for desalination. Also disclosed is an at-line sensor utilizing the fluorescence based extracellular enzyme activity assay that is positioned in the membrane filtration system for detection of biofouling.

19 Claims, 24 Drawing Sheets

(58) Field of Classification Search
USPC .......................................................... 73/61.62
See application file for complete search history.

(56) References Cited

U.S. PATENT DOCUMENTS

| | | | |
|---|---|---|---|
| 6,699,684 B2* | 3/2004 | Ho | B01D 61/04 |
| | | | 435/29 |
| 2003/0032080 A1* | 2/2003 | Schabert | G01N 33/533 |
| | | | 536/8 |
| 2009/0045144 A1* | 2/2009 | Cohen | B01D 65/08 |
| | | | 210/745 |
| 2011/0130306 A1* | 6/2011 | Chang | C07F 5/025 |
| | | | 549/213 |
| 2013/0220002 A1 | 8/2013 | Kobayashi et al. | |
| 2018/0326329 A1* | 11/2018 | Collins | B01D 29/668 |

OTHER PUBLICATIONS

International Search Report in corresponding/related International Application No. PCT/IB2017/055042, dated Nov. 8, 2017.
Romaní, A.M., et al., "Relevance of Polymeric Matrix Enzymes During Biofilm Formation," Microbial Ecology, Jan. 29, 2008, vol. 56, No. 3, pp. 427-436, Springer-Verlag, NE.
Written Opinion of the International Searching Authority in corresponding/related International Application No. PCT/IB2017/055042, dated Nov. 8, 2017.
Communication pursuant to Article 94(3) EPC in corresponding/related EP Application No. 17771579.4, dated Mar. 1, 2022.

* cited by examiner

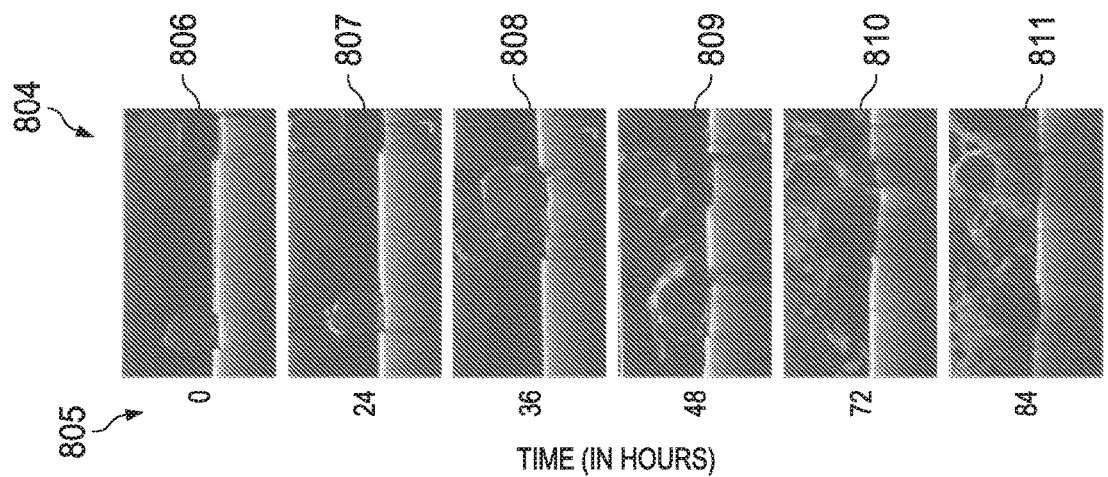
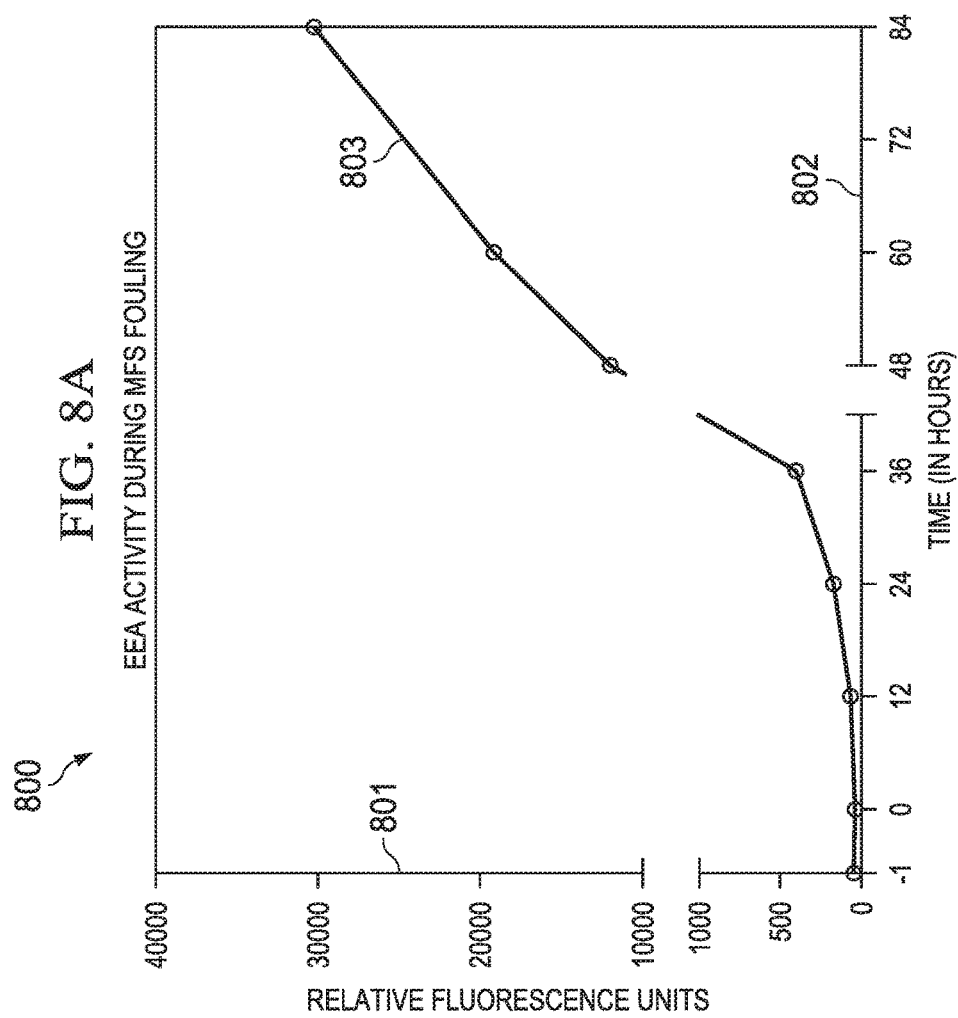
FIG. 8A
FIG. 8B

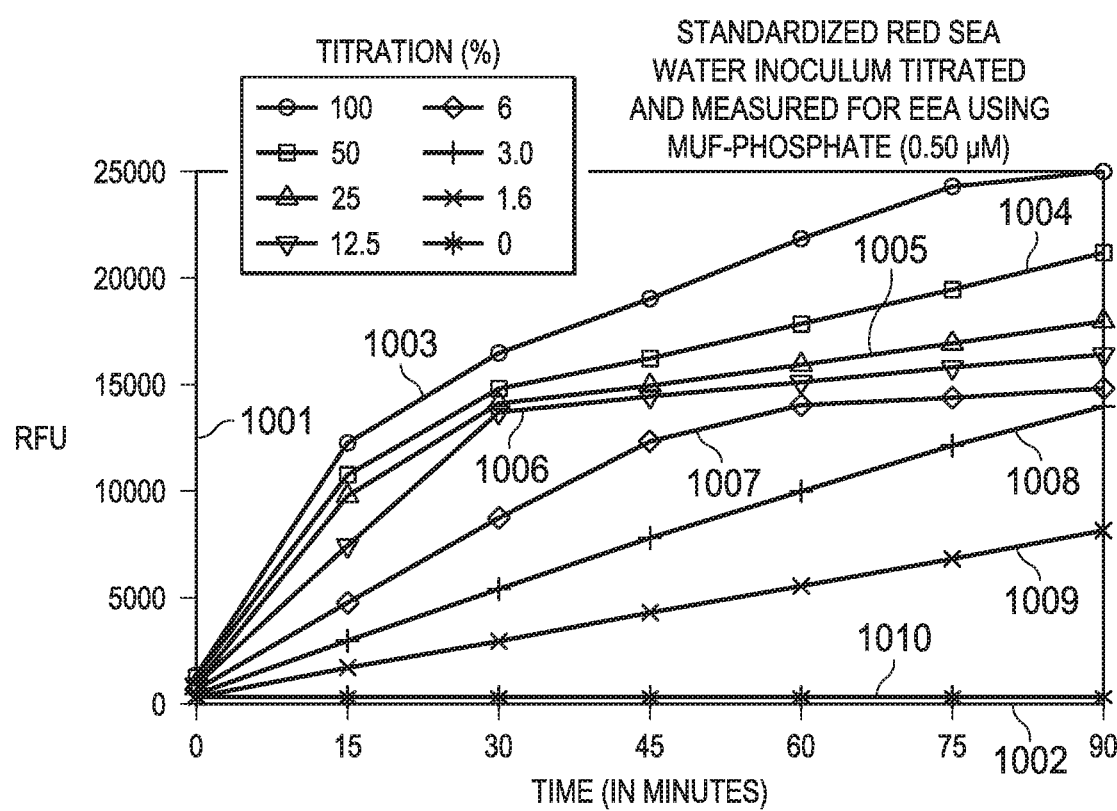

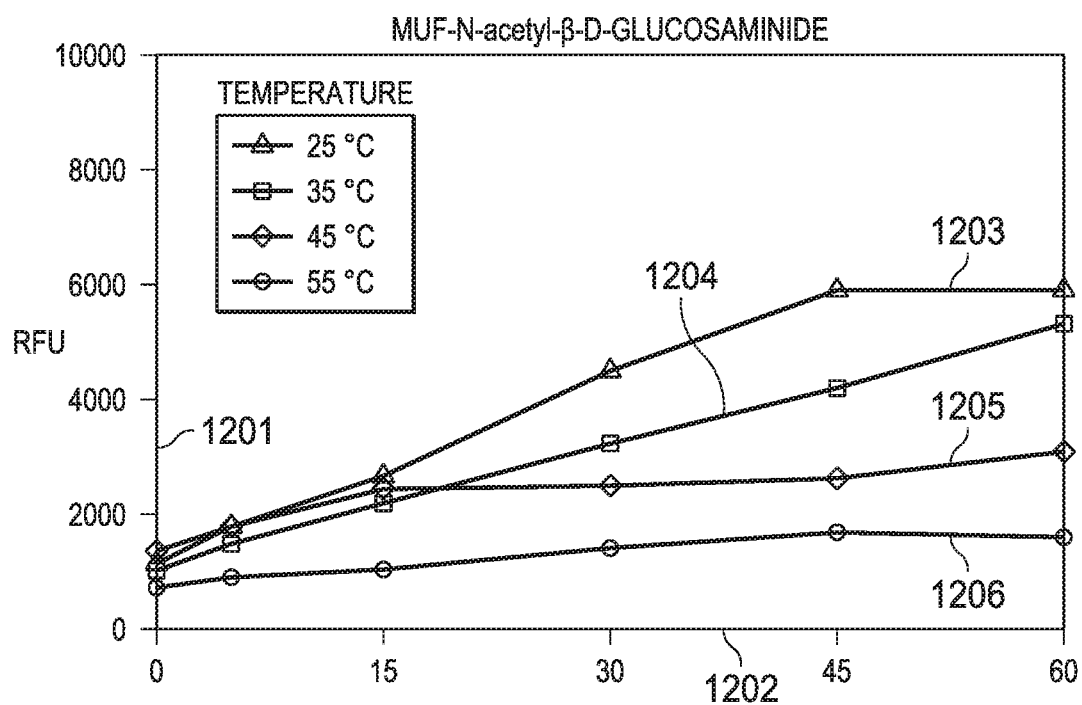
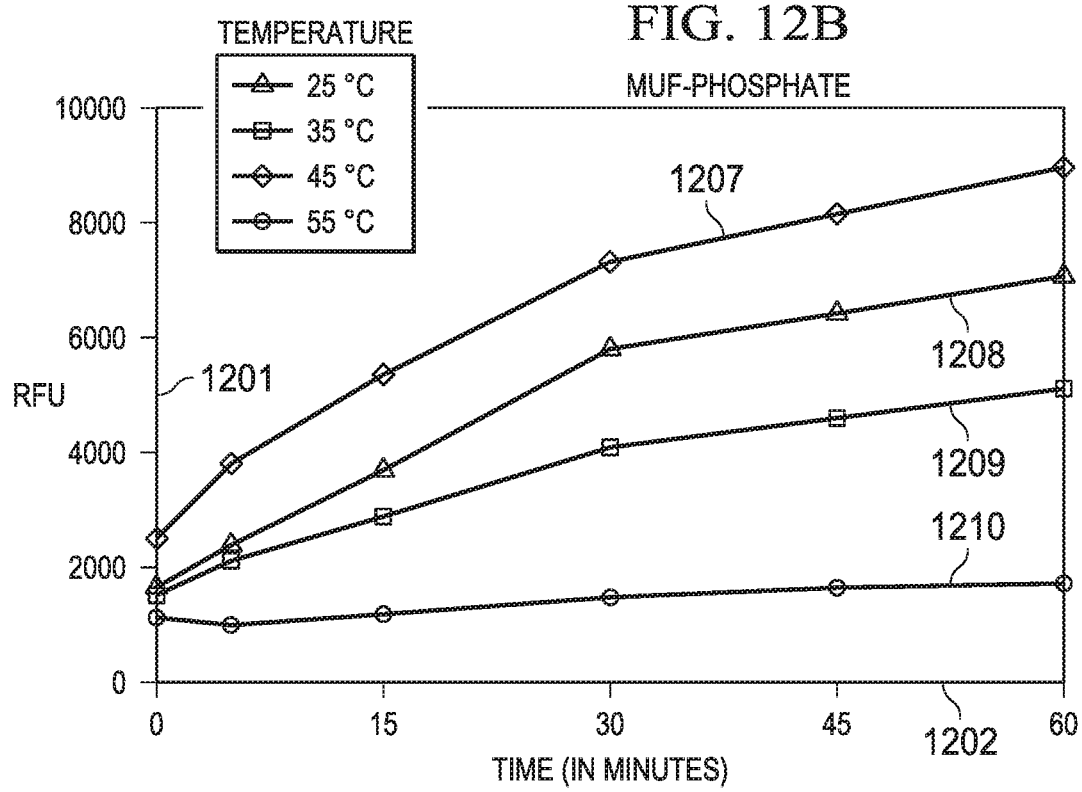

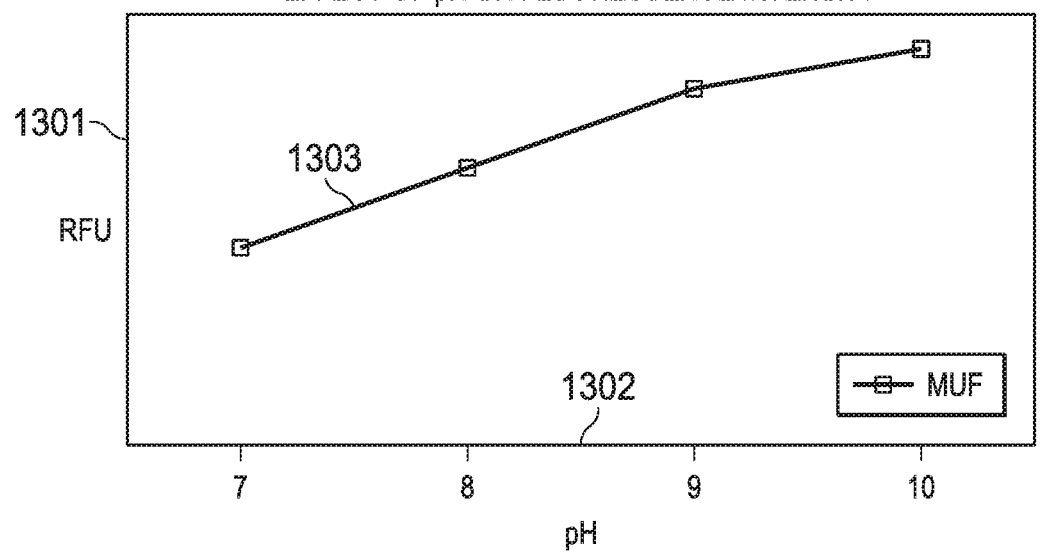
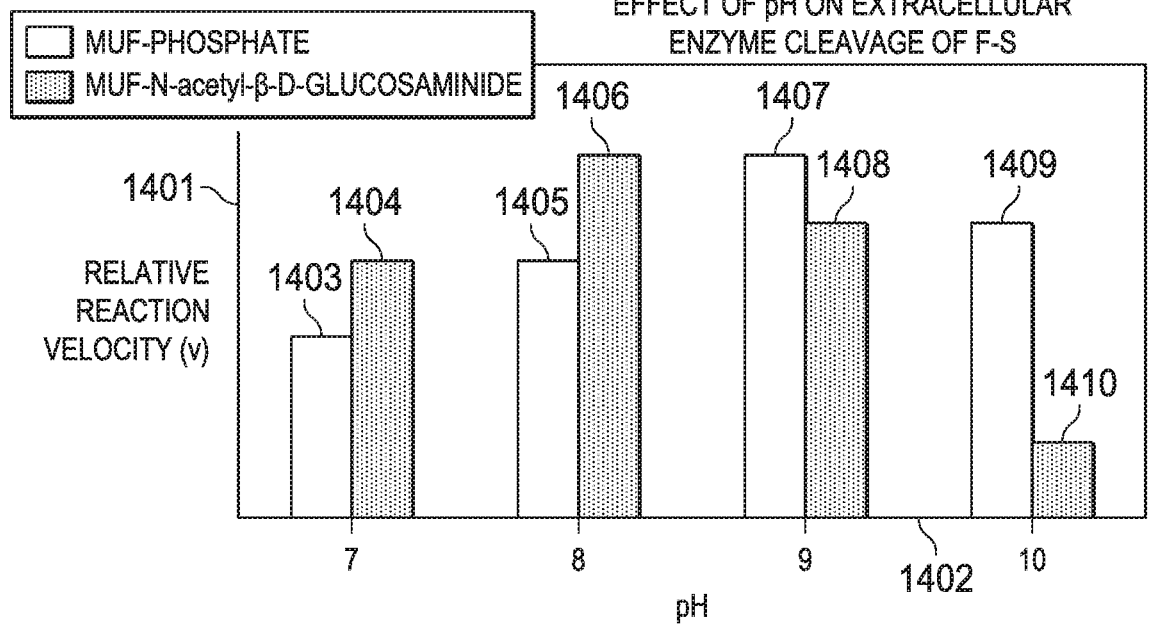

FLUORESCENCE BASED EXTRACELLULAR ENZYME ACTIVITY ASSAY FOR EARLY DETECTION OF BIOFOULING IN SEAWATER DESALINATION SYSTEMS

RELATED APPLICATION DATA

This application is a U.S. National Stage Application of International Application No. PCT/IB2017/055042, filed on Aug. 21, 2017, which claims the priority and benefit of U.S. Provisional Patent Application Ser. No. 62/453,708, filed Feb. 2, 2017, the entire contents of which are incorporated herein by reference.

TECHNICAL FIELD

The present invention relates to a method for detection of biofouling in seawater desalination systems using a fluorescence based extracellular enzyme activity assay.

BACKGROUND OF THE INVENTION

The background of this invention will address water desalination, membrane technology, biofouling, and extracellular enzyme activity assay.

Water Desalination

Global population increases projected over the next decades will require water and energy for domestic, agricultural and industrial consumption, all of which ultimately rely on a rapidly diminishing global water supply. With water use expected to grow by twice the rate of population growth, a 2013 United Nations report estimates that by 2050 most countries around the world will experience water stressed conditions. A real need exists to discover alternative sources of water and adopt stricter water reclamation processes in safe, economical and efficient ways. According to a United States Geological Survey report approximately 97% of the Earth's water is saline, and as such, water filtration technology plays a critical role in opening up previously unusable water sources.

The desalination process removes minerals from saline water, such as seawater, to produce water that is suitable for human or agricultural uses. Most of the interest in desalination focuses on production of fresh water for consumption and is particularly of interest in areas where seawater is abundant, but fresh water sources or rainwater may be limited. However, desalinating seawater can be costly because a large amount of energy is consumed in the process.

There are a number of means known for desalinating water, including distillation and evaporation, but the most prevalent is the use of reverse or forward osmosis membrane filtration utilizing membranes that allow water to permeate through the membrane while preventing minerals and salts from passing through the membrane.

Membrane Technology

A membrane is a selective barrier that with a partial permeability—it will allow certain substances to pass through the barrier, but prevent other substances from doing so. A membrane is usually defined by a discrete, thin interface that moderates the permeation of chemical species in contact with it. The substances that can pass through, or be prevented from passing through, the membrane interface may be molecules, ions or other small particles. The influent of an artificial membrane is known as the feed-stream, the liquid that passes through the membrane is known as permeate, and the liquid containing the retained constituents (substances that are prevented from passing through the membrane) is the retentate or concentrate. A normal filter meets this definition of a membrane, but, by convention, the term membrane is usually limited to structures that permeates dissolved or colloidal species, whereas the term filter is used to designate structures that separate larger-sized particulate suspensions.

Membranes can be generally classified into two classes: synthetic membranes and biological membranes. Biological membranes include cell membranes (outer coverings of cells or organelles that allow passage of certain constituents), nuclear membranes, which cover a cell nucleus, and tissue membranes, such as mucosae or serosae. Synthetic membranes are made by humans for use in laboratories or industry, such as chemical plants.

The degree of selectivity of a membrane depends on the membrane pore size. Depending on the pore size, they can be classified as microfiltration (MF), ultrafiltration (UF), nanofiltration (NF) and reverse osmosis (RO) membranes. Membranes can be neutral or charged, and particle transport can be classified as active transport or passive transport. Active transport of permeate can be facilitated by pressure, concentration, chemical or electrical gradients of the membrane process.

Electrically charged membranes can be dense or microporous, but are most commonly microporous with pore walls that carry fixed positively or negatively charged ions. A membrane with positively charged ions is referred to as an anion-exchange membrane because it binds anions in the surrounding fluid. Similarly, a membrane containing negatively charged ions is called a cation-exchange membrane. In a cation-exchange membrane, the fixed anions are in electrical equilibrium with mobile cations in the interstices of the polymer. On the contrary, the mobile anions are more or less completely excluded from the cation-exchange membrane because of their electrical charge, which is identical to that of the fixed ions.

Membrane separation with a charged membrane interface is achieved primarily by exclusion of ions of the same charge as the fixed ions of the membrane structure, and to a much lesser extent by the pore size. Due to the exclusion of the anions, a cation exchange membrane permits transfer of cations only. Anion exchanger membranes carry positive charges fixed on the polymer matrix. Therefore, they exclude all cations and are permeable only to anions.

The advent of advanced membranes for water desalination within the last two decades and subsequent technological breakthroughs in design has increased membrane energy efficiency and performance. As a result, higher quality potable water has been produced. However, a major cost associated with membrane based operational failure results from biological fouling (biofouling), occurring in over 40% of Reverse Osmosis (RO) desalination plants. In spite of this, biofouling is largely treated using generic, arbitrary and un-guided cleaning protocols.

Current methods to guide membrane cleaning rely on measuring physical changes to specific operational parameters. For example, reductions of the permeate yield by 10% or increases in either feed pressure or trans-membrane pressure (TMP) by ~15%, prompt cleaning. These physical parameters have been linked to increased microbial quantities and metabolic activity. Operational changes resulting from bacterial biofouling are often caused by maturation of bacterial communities, which are inherently tolerant to cleaning mechanisms, resulting in poor restoration of membrane function with current approaches. A deeper understanding of how bacterial colonization leads to the loss of membrane efficiency and function is important to guide maintenance protocols for water systems during biofouling.

Biofouling

Microorganisms are microscopic living organisms that are found in all areas of the biosphere in enormous numbers. Bacteria make up a large portion of these microorganisms and are among the most abundant organisms on earth. Bacteria possess a wide range of metabolic versatility and adaptability allowing them to thrive in many circumstances where other organisms could not survive.

Bacteria can exist as individual organisms, but the majority will live in colonies consisting of an aggregation of numerous bacterial organisms. One of the mechanisms employed by bacterial colonies, as well as other microorganisms, is the production of extracellular polymeric substances that produce a slime-like covering over the colonies. These aggregated microorganisms usually exist in nature by attaching to and growing upon living or inanimate surfaces. A common feature of this attached aggregated growth state is that the cells develop a biofilm. Biofilm formation is a process whereby microorganisms attach to and grow on a surface and produce extracellular polymers that facilitate attachment and matrix formation.

A biofilm is a bacterial aggregation on a surface with a structure that includes bacterial cells and a matrix of bacterially produced extracellular polymeric substances (EPS), along with biogenic and inorganic particles. Extracellular polymeric substances EPS, which are primarily composed of proteins, polysaccharides, and nucleic acids, plays a vital role in biofilm growth and development. As a result, the extracellular polymeric substances EPS can alter the density, porosity, charge, water content, and sorption properties of the biofilm with time.

Additionally, extracellular polymeric substances (EPS) enhance the mechanical strength and adhesiveness of the biofilm through electrostatic attraction, hydrogen bonding and London dispersion forces. Thus, biofilm structural integrity, adhesiveness and elasticity make biofilms resilient and difficult to remove from surfaces. The presence of divalent cations, such as magnesium and calcium, can form salt bridges, for example, between negatively charged bacteria and a surface such as a membrane surface. The structure and charges of the biofilm and the EPS thus help to protect the aggregated bacteria or other microorganisms from applied biocides.

Biofouling is the gradual accumulation of organisms on surfaces to the detriment of the function of the surface, and of particular relevance herein are those organisms that produce biofilms. Biofilm formation is caused by the accumulation of microorganisms and extracellular polymeric substances (EPS) produced by the microorganisms. Biofilms can form on a variety of surfaces including membranes (e.g., in membrane filtration systems), heat exchangers, medical devices, paper manufacturing systems, food processing systems, and in underwater construction. Biofilm formation, which occurs frequently in membrane filtration systems, causes biofouling, which is an unacceptable decline in membrane performance. Additionally, a hydrodynamic boundary layer generally exists adjacent to the biofilm which reduces the flow of the feed water over the biofilm, thereby decreasing the ability of the feed water to dislodge the biofilm.

Bacteria are prevalent in both abiotic and biotic environment as free-floating planktonic cells and sessile communities. Historically, bacteria have been represented as single-cell planktonic organisms. Only in the last fifty years have bacteria been associated with complex biological systems, termed biofilms, as their predominate state. In environments where bacteria are subject to high shear forces, such as those environments found in natural streams or industry membrane modules, bacteria have evolved to adhere and populate a variety of surfaces.

Adherence of planktonic bacteria leads to the rise of clusters of bacteria, referred to as microcolonies. Microcolonies mature into biofilms with accumulation of an encapsulating layer consisting of polysaccharides and proteinaceous exopolymers serving to protect the community from physical and environmental stress. Eventually, groups of cells from within the biofilm can disperse to colonize adjacent surfaces.

These mechanisms therefore propagate formation of biofilm on filtration membranes of all types, reducing membrane performance and ultimately leading to membrane damage. Membrane fouling incurs costs that are often beyond just replacement of the membrane module. Economic loss can be extended to include unsuccessful chemical and biocide application, reduced production as a result of interruptions for shut-down and start-up, and the cost of man hours required to resolve the problem, all of which have been estimated at 30% of operating cost. Choosing to clean before the problem is exacerbated therefore is critical, and can be informed by techniques that measure biological activity non-invasively, in a rapid and sensitive manner. One such method involves using bacterial catabolism to determine the number of bacteria present within a system.

Extracellular Enzyme Activity Assay

One means of using bacterial catabolism to determine bacterial presence is through assaying the fluid medium associated with the membrane for extracellular enzyme activity. Bacteria use enzymes to breakdown substances in the environment to produce materials required for their metabolic processes. These enzymes are either associated with the bacterial membrane or secreted by the bacteria into the bacterial environment and can be detected in the fluid medium around the bacteria. One of the assays useful for detecting theses enzymes uses fluorescing chemicals, such as fluorogen substrates, to determine the amount of bacterial activity present by measuring the level of fluorescence produced from cleavage of the of the fluorogen substrates by the extracellular enzymes.

Planktonic bacteria in the natural environment, specifically aquatic bacteria, have been extensively studied for elucidation of their role in the cycling of nutrients during ecological processes. Since bacteria rely on obtaining crucial nutrients from the surrounding milieu in aquatic environments, a wide variety of enzymes are used to hydrolytically cleave dissolved natural organic materials (NOM) to provide substrate materials for respiratory and metabolic function. Enzymes that interact with extracellular materials are attached to the bacterial membrane (ecto-enzymes) or secreted (exo-enzymes), and are collectively referred to as extracellular enzymes.

As bacteria secrete a set of ubiquitous extracellular enzymes to hydrolyze substrates, bacterial enzymatic activity can be realized using a substrate bound to a fluorogenic molecule. Enzymes cleaving the substrate fluorogen bond liberate fluorogen molecules that can be measured using a simple fluorometer. This measurement is referred to as Extracellular Enzyme Activity (EEA) and has been used to gauge bacterial dynamics in both a rapid and sensitive fashion. EEA measurements can therefore be adapted for use within an at-line "sensor," attached proximally upstream of a seawater desalination membrane module, to monitor membrane fouling state. Prognostically, the system can guide anti-bacterial fouling strategies caused by bacterial biofilm formation.

Monitoring of membrane health is essential in operation to determine relevant preventative action and corrective action. Active monitoring of the membrane status provides the opportunity for the development of tailored responses to foulants. A number of common and exploratory analytical tools and techniques for detection of bacteria have been used over the years with varying degrees of success.

Measurement of Colony Forming Units (CFU) is a slow tedious process that can take upwards of 18 hours to complete and the observations are often subjective. Measurement of Light Scattering is continuous type of monitoring, but has a low level of sensitivity and a high risk of false positives. ATP Luminescence is a quick method for indicating biomass activity, but the presence of non-microbial ATP can cause false-positive readings. Flow-Cytometry Measurements can measure the presence of cells, but tend to underestimate the counts due to cell-clustering, and may also be difficult to use because seawater can cause interference with the dyes required for the method. Polymerase Chain Reaction (PCR) measurements can be used, but the sample processing time prior to the testing procedure is long and naturally occurring substances can interfere with the readings. Immunoassays have been used because the assays are relatively fast, but they are not quantitative and cross-reactivity is a problem. Assays using Fluorogen Substrates are promising because the assays are relatively fast, and can detect bacterial biofilms; however, the assay sensitivity is substrate dependent needing further characterization.

Although there are limitations to each of the methods summarized above, a need exists to develop a flexible prognostic tool for biofouling study. The field of biology has witnessed rapid technological advance, spurred by coupling engineering with systems biology, resulting in the genesis of synthetic biology. Synthetic biology has expanded the molecular toolkit to control and program cellular behavior. The clear winner is therefore biotechnology, which has been a hotbed for innovation. Molecules for probing populations and single cells with high specificity are now available, and a libraries of fluorogen molecules conjugated to substrates have been generated that can be applied to measure bacterial enzyme activity. Enzyme kinetics determinations have been correlated to bacterial quantitates. Hence, the Fluorogen-Substrate (F-S) system can be adapted for use in membrane biofouling monitoring.

Bacterial extracellular enzymes are responsible for catalyzing substrates external to the cell. Enzyme activity can be limited in range to the environment adjacent to the cell membrane by being tethered to the membrane (exo-enzyme), or can be secreted to act locally in the microenvironment (ecto-enzyme). In essence, bacterial extracellular enzymatic activity increases the conversion of large organic molecules into intermediate molecules in the surrounding environment that can then be readily transported via active transport into the cell. Measurements of the hydrolytic cleavage of fluorogen-substrates mediated by extracellular enzymes is one means of detecting and quantifying the presence bacterial activity.

From the 1960's and onward, researchers have measured extracellular enzyme activity to assess nutrient cycling in waters, soil and sediments. More recently, a number of commercially available fluorogen compounds have been conjugated with substrates readily catalyzed by bacteria. As seen in Table 1, fluorescence detection has been used with high sensitivity for quantification of bacteria based on enzymatic measurement of fluorogen substrate cleavage in soil and water samples. Table 1 shows fluorogen substrates used to measure bacteria from soil and aquatic sources, with abbreviations: MUF being 4-methylumbelliferone, and AMC being 7-amino-4-methyl coumarin.

TABLE 1

| Sample Type | Fluorogenic Substrates |
| --- | --- |
| Soil | L-Arginine-AMC |
| | L-Leucine-AMC |
| | L-Tyrosine-AMC |
| | MUF-7-$\beta$-D-xyloside |
| | MUF-$\alpha$-glucoside |
| | MUF-acetate |
| | MUF-$\beta$-D-cellobiose |
| | MUF-$\beta$-D-galactoside |
| | MUF-$\beta$-D-glucoside |
| | MUF-$\beta$-D-glucuronide |
| | MUF-heptanoate |
| | MUF-N-acetyl-$\beta$-glucosaminide |
| | MUF-phosphate |
| | p-nitrophenyl phosphate |
| Marine & Fresh water | 5-cyano-2,3-ditolyl tatrazolium chloride |
| | $\beta$-naphythylamine |
| | L-Leucine-AMC |
| | L-Leucine-AMC |
| | L-Leucine-p-nitroanilide |
| | MUF-$\beta$-D-galactosidase |
| | MUF-$\beta$-D-glucopyranoside |
| | MUF-$\beta$-D-glucuronide |
| | MUF-hexose |
| | MUF-n-acetyl-$\beta$-D-glucosaminide |
| | MUF-Phosphate |

Bacterial biofouling is operationally defined, resulting from the negative impact of bacterial biofilms and microbial products on membrane filtration systems. Biofilm formation is often associated with increased quantities of bacteria. Monitoring the activity of bacteria localized to the membrane surface using a rapid and sensitive measurement can guide cleaning processes and determine the most suitable time to initiate cleaning. Currently there exists a gap between initiation of biofilm formation and start of biofouling corrective action. Development of an early monitoring system that can be used at-line and elucidation of a biofouling risk index based on fluorescent-based extracellular enzyme activity measurements can be practical in bridging the gap.

Biofilm formation and development has become problematic in both academic and industrial settings because of its role in the efficiency in system processes. Successful fluorescent measurement of EEA in an at-line sensor would provide the pre-fouling monitoring required to guide successful membrane cleaning in water desalination systems. Inevitably, a prognostic approach will reduce costs, extend membrane life directly by limiting fouling and indirectly by reducing overexposure to chemicals, and provide increased high quality water for consumption to meet the growing demands of a developing world. Prognostically, the system can guide anti-bacterial fouling strategies caused by bacterial biofilm formation.

SUMMARY OF THE INVENTION

Provided herein are methods of using fluorescent measurements of fluorogen-substrate cleavage by extracellular enzymes to monitor bacterial colonization proximal to the surface of filtration membrane systems in a rapid and non-invasive manner. Biological fouling is operationally defined, resulting from the negative impact of bacterial colonization activity on industrial systems. Currently there exists a detection gap between bacterial colonization and initiation of biofouling. Since bacteria in aquatic environments produce extracellular enzymes to catalyze large molecules into assimilable molecules, fluorogen bound bacterial substrates can be used to measure extracellular enzyme activity (EEA).

Also disclosed herein is an at-line sensor for use in a membrane filtration system utilizing the method of fluorescent measurement of fluorogen-substrate cleavage by extracellular enzymes to monitor bacterial colonization proximal to the surface of filtration membrane systems in a rapid and non-invasive manner.

Enzymes that interact with extracellular materials are attached to the bacterial membrane (ecto-enzymes) or secreted (exo-enzymes), collectively referred to as extracellular enzymes. As bacteria secrete a set of ubiquitous extracellular enzymes to hydrolyze substrate, bacterial enzymatic activity can be realized using a substrate bound to a fluorogenic molecule. Enzymes cleaving the substrate fluorogen bond liberate fluorogen molecules that can be measured using a fluorometer. This measurement is referred to as Extracellular Enzyme Activity (EEA) and has been used to gauge bacterial dynamics in both a rapid and sensitive fashion. EEA measurements can therefore be adapted within an at-line "sensor," attached proximally upstream of a seawater desalination membrane module, to monitor membrane fouling state. Prognostically, the system can guide anti-bacterial fouling strategies caused by bacterial biofilm formation.

The present invention is a method for detecting membrane fouling comprising the steps of: providing a membrane fouling sensor positioned adjacent to a feed solution stream in a membrane filtration system wherein a portion of a feed solution stream flows through the sensor contacting a membrane therein; said membrane fouling sensor having an inlet valve directing the feed stream to the sensor and an outlet valve directing the feed stream from the sensor unit back to the main feed stream proximal to the main filtration unit; allowing the feed solution stream to contact the membrane fouling sensor during the normal operation of the membrane filtration system, such that the sensor membrane is subject to substantially the same conditions as the membrane in the membrane filtration unit; operating the membrane filtration system to for a time period ranging from 1 hour to 100 hours, during which time the sensor membrane and the membrane in the membrane filtration unit are exposed to any microorganisms in the feed solution stream and said microorganisms may adhere to the sensor membrane causing one or more biofilm to develop on the membranes and producing extracellular enzymes; creating a closed system in the membrane fouling sensor by closing the inlet and outlet valves thereby trapping a portion of the feed stream and any microbial extracellular enzymes in the membrane fouling sensor; injecting a fluorogen-substrate into the membrane fouling sensor via an inject port positioned distal to the inlet valve and proximal to the membrane; allowing the fluorogen-substrate to contact the feed stream and any microbial extracellular enzymes trapped in the sensor for 1-60 minutes; removing a portion of the feed stream trapped in the sensor via the flush port; using a fluorometer to measure the removed portion of the feed stream for fluorescence produced from the fluorogen-substrate interaction with extracellular enzymes; correlating the measured fluorescence with extracellular enzyme activity in the sample; and using the correlation to determine a biofouling level of the membranes.

The present invention also includes a method wherein the membrane in the sensor unit is comparable to the membrane in the main membrane filtration unit such that the membrane in the sensor experiences substantially the same conditions as the membrane in the main membrane filtration unit, wherein the step of flushing the closed membrane fouling sensor of fluorogen-substrate by injecting a cleaning solution via the inject port and removing the cleaning solution via the flush port, further comprising the step of opening the inlet and outlet valves to allow feed stream solution to flow through the membrane fouling sensor, wherein the membrane filtration system is used for desalination of the feed stream sample, wherein the fluorogen substrate comprises Methylumbelliferone (MUF), and, wherein the MUF fluorogen substrate is selected from MUF-phosphate, MUF-N-acetyl-β-D-glucosaminide, MUF-heptanoate and MUF-β-D-glucopyranoside.

The present invention is a membrane fouling sensor having a sensor unit positioned adjacent to a main feed solution stream proximal to a main membrane filtration unit in a membrane filtration system, said sensor unit having a filtration membrane; an inlet valve positioned at the main feed stream that diverts a portion of the main feed stream to the sensor unit as a sensor feed stream when opened and prevents the main feed stream from entering the membrane fouling sensor when closed; an outlet valve that directs the sensor feed stream back to the main feed stream distal to the inlet valve and proximal to the main membrane filtration unit when opened and retains the sensor feed stream in the membrane fouling sensor when closed, a feed stream conduit positioned between the inlet valve and the outlet valve that directs the feed stream from the inlet valve to the outlet valve through the sensor unit, an inject port in the feed stream conduit distal to the inlet valve and proximal to the sensor unit; and a flush port in the feed stream conduit distal to the sensor unit and proximal to the outlet valve.

The membrane fouling sensor also includes an inlet valve and the outlet valve can be closed trapping the sensor feed stream in the conduit and sensor unit, one or more solution can be injected into the membrane fouling sensor via the inject port, one or more solution is a fluorogenic-substrate that can be cleaved by one or more extracellular enzymes solutions, wherein a portion of the sensor feed stream can be removed via the flush port, wherein the conduit and sensor can be flushed of materials by injecting a solution in through the inject port and removing the solution through the flush port, wherein the membrane in the sensor unit is comparable to the membrane the main membrane filtration unit such that the membrane in the sensor experiences substantially the same conditions as the membrane in the main membrane filtration unit, and wherein the membrane in the membrane filtration system is selected from membranes for microfiltration, ultrafiltration, nanofiltration, reverse osmosis or forward osmosis.

The details of one or more embodiments are set forth in the description below. As used throughout, the methods are described for use in membrane filtration systems, but the methods described in the present invention may also be useful in any system or surface where there is biofilm formation and measurement of Extracellular Enzyme Activity is desired. Other features, objects, and advantages will be apparent from the description and from the claims.

BRIEF DESCRIPTION OF THE DRAWINGS

The above, and other objects and advantages of the present invention will be understood upon consideration of the following detailed description taken in conjunction with the accompanying drawings, in which like reference characters refer to like parts throughout, and in which:

FIG. 8A is a graph of extracellular enzyme activity (EEA) signal measured by cleavage of fluorogen MUF;

FIG. 8B is a representation of MFS fouling using OCT corresponding to the time of the graph in FIG. 8A;

FIG. 10 is a graph of fluorogen-substrate signal titrations;

FIGS. 12A and 12B are graphs showing temperature dependence for fluorescence;

FIG. 13 is a graph of the effect of pH on fluorescence;

FIG. 14 is a bar graph of the effect of pH on extracellular enzyme cleavage of fluorogen substrates;

DETAILED DESCRIPTION

As described herein, the present invention discloses methods for early detection of membrane biofouling using a fluorogen-substrate based Extracellular Enzyme Activity (EEA) assay, and discloses a sensor for use in a membrane filtration system utilizing a fluorogen-substrate based Extracellular Enzyme Activity (EEA) assay detection means.

Presented herein is a high-throughput fluorometric enzyme-based activity assay using a seawater matrix to characterize commercially available fluorogen-substrates for extracellular enzyme activity. Fluorogen and fluorogen bound to substrate were characterized at pH (7-10) and temperature (15° C.-55° C.) for determination of the effect on both fluorogen and corresponding enzyme activity. Both the fluorogen and substrate catalysis are dependent on pH and temperature with different sensitivity ranges. Two fluorogen-substrates were subsequently down-selected based on compatibility with water obtained from the Red Sea for use in testing of a modified flow-cell sensor to track biological fouling of a desalination membrane unit.

In a first embodiment, the method disclosed herein is a fluorogen-substrate based Extracellular Enzyme Activity (EEA) assay for early detection and quantification of bacterial colonization activity based on the presence of bacterial extracellular enzymes present in the fluid medium around the membrane. As described herein, the method is useful for detecting and quantifying membrane biofouling in water filtration systems, but the method can be used in other applications where biofouling may occur. The method described herein is particularly advantageous when used in water desalination systems. Reverse osmosis membrane and forward osmosis membrane filtration systems are the most efficient systems for water desalination, but the method herein may be used with other types of membrane filtration systems that are subject to biofouling. The proposed approach is aimed at optimizing standard cleaning regiments by providing near-real-time data on biological bacterial activity. The present invention EEA assay for early detection can be used to holistically measure the system since the reaction occurs in the bulk liquid, which is highly advantageous over traditional imaging techniques that are both invasive (require viewing panes) and are limited in application due to highly localized nature of imaging at the macro level.

FIGS. 1A-1D show biofouling in place on 4 types of membranes. The bacterial growth can be seen as dark or glossy spots on the surface or embedded in the membrane pores. By the time bacterial biofilms reach the visually distinguishable point, reduction in membrane flow is already significant. Early detection of biofouling decreases operating costs, increases operating efficacy, extends the life of the membranes, and increases the quality of the useable water produced via the desalination method.

Figure 1A:
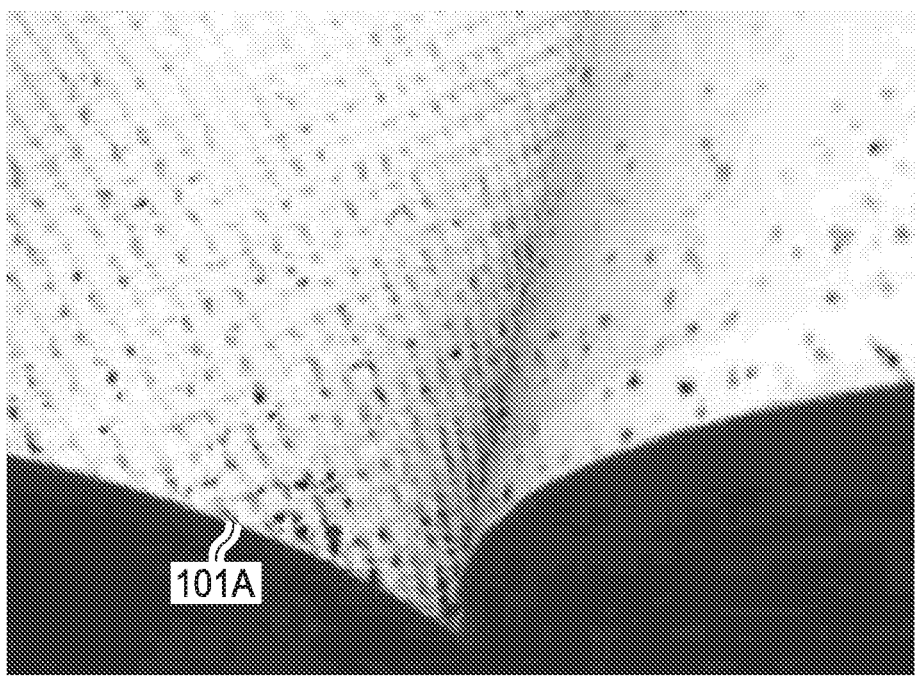
FIGS. 1A-1D are examples of fouled membranes.
Figure 1B:
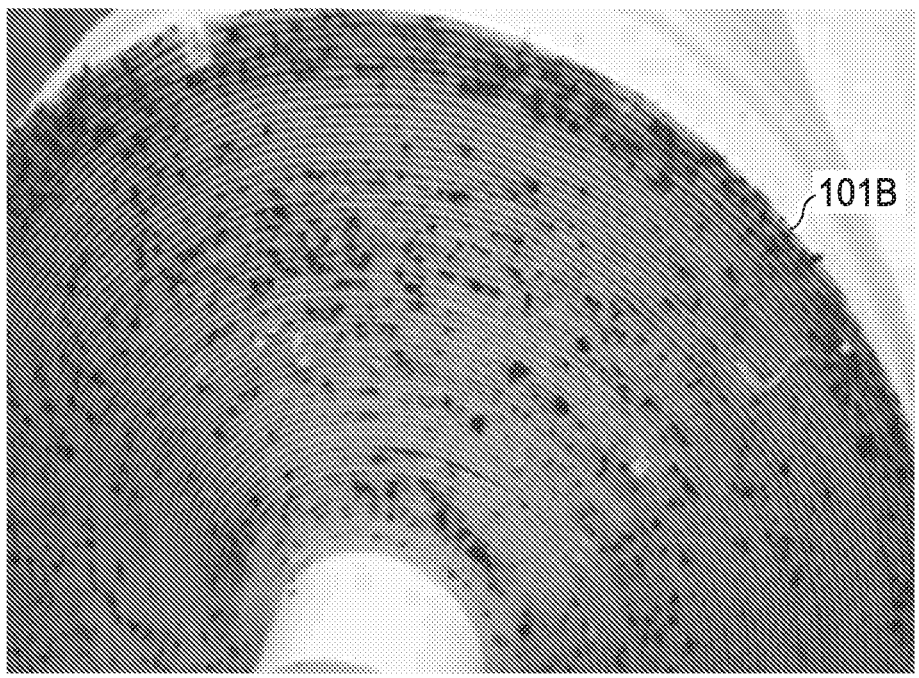
Figure 1C:
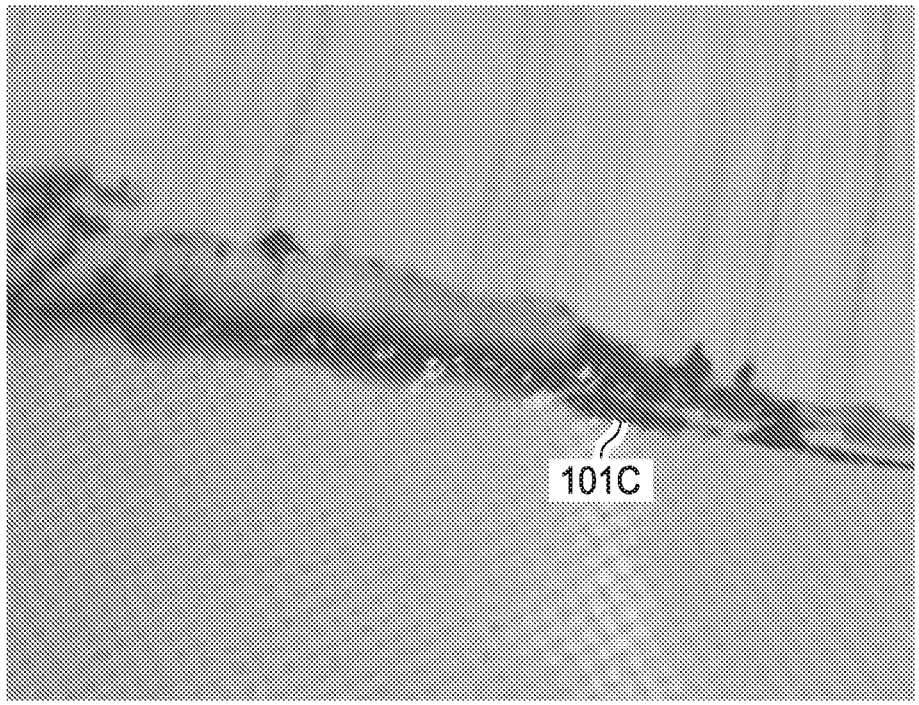
Figure 1D:
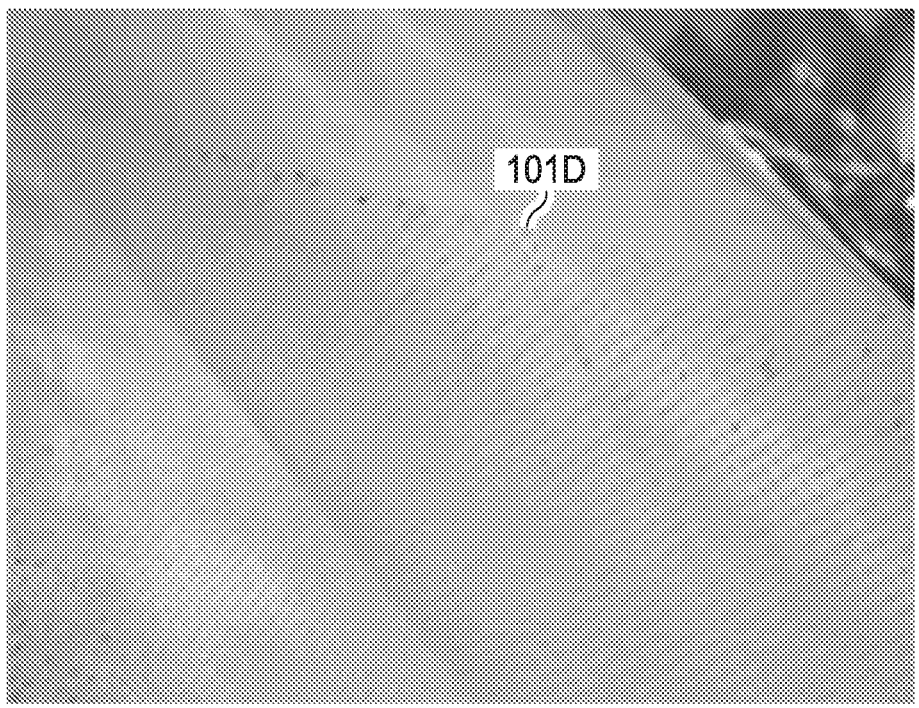
Figure 2:
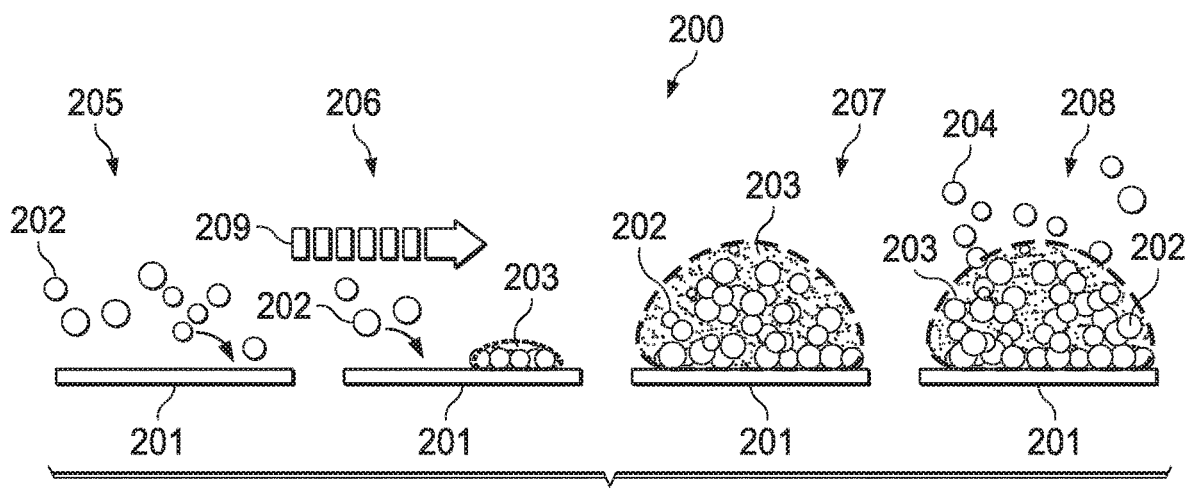
FIG. 2 is a schematic illustration of biofilm formation.

FIG. 2 is a schematic of biofilm development 200 on a membrane surface 201 with bacterial growth generally following a directional path indicated by arrow 209. In Stage 1 (205), planktonic bacteria 202 begin to adhere to the surface of the membrane 201. In Stage 2 (206), the planktonic bacteria 202 lead to the rise of clusters of bacteria, referred to as colonies or microcolonies 203, depending on the colony size. In Stage 3 (207), as the microbial growth continues, the microcolonies 203 mature into larger colonies in biofilms with accumulation of an encapsulating layer consisting of polysaccharides and proteinaceous exopolymers serving to protect the community from physical and environmental stress. Stage 4 (208) is characterized by groups of bacterial cells from within the biofilm dispersing 204 to colonize adjacent surfaces. The growth of these bacterial colonies leads to biofouling of the membrane surface 201, and consequently, a reduction in the membrane function. Bacteria organisms are primarily decomposers, and the bacteria in the biofilms will produce enzymes that breakdown substances in the surroundings to produce materials for the bacterial metabolism.

Figure 3A:
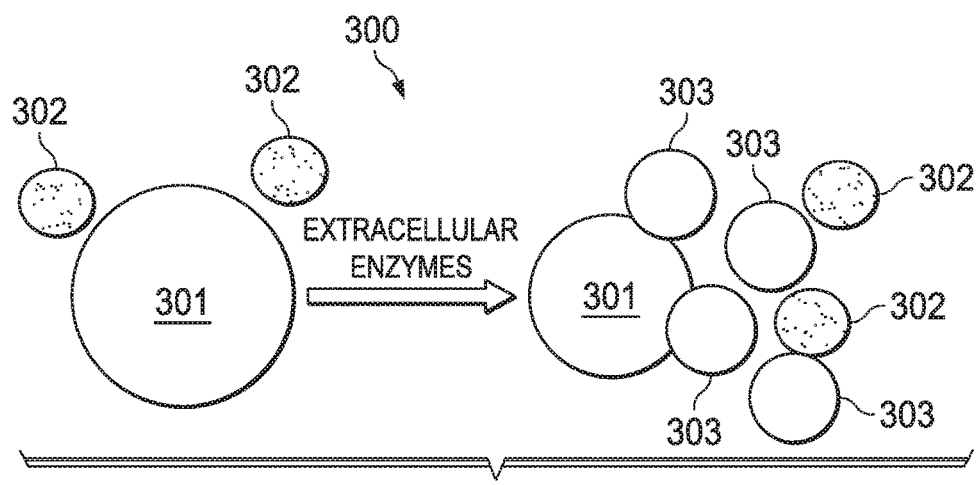
FIG. 3A is a schematic of bacteria in an aquatic environment.
Figure 3B:
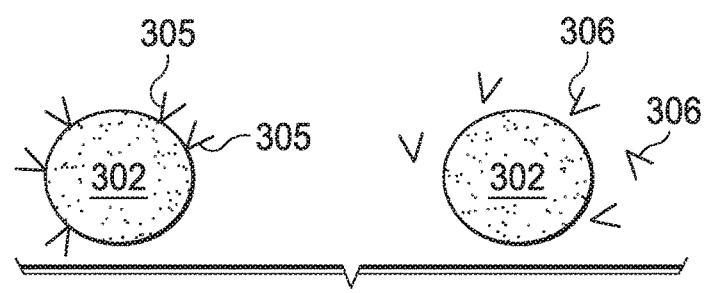
FIG. 3B is a representation of ecto-enzymes and exo-enzymes in the environment of FIG. 3A.

FIG. 3 represents the hydrolytic cleavage of fluorogen-substrate mediated by extracellular enzymes by bacteria in an aquatic environment 300. Bacteria 302 will produce enzymes to breakdown the natural organic molecules 301 (NOM) around them and the action of the enzymes 304 will lead to the production of assimilible molecules 303 that can be used by the bacteria 302. Enzyme activity can be limited in range to the environment adjacent to the cell membrane by being tethered to the membrane as an ecto-enzyme 305, or can be secreted to act locally in the microenvironment as an exo-enzyme 306. In essence, bacterial extracellular enzymatic activity increases the conversion of large organic molecules 301 into intermediate molecules 303 in the surrounding environment that can then be readily transported via active transport into the bacterial cell 302. These enzymes can be detected and quantified in the fluid medium that surrounds the bacterial cells and provide an indication of the level of bacterial activity. When a fluorogen substrate is used in the detection assay, the level of measurable fluorescence corresponds to the level of enzyme present in the system.

Figure 4A:
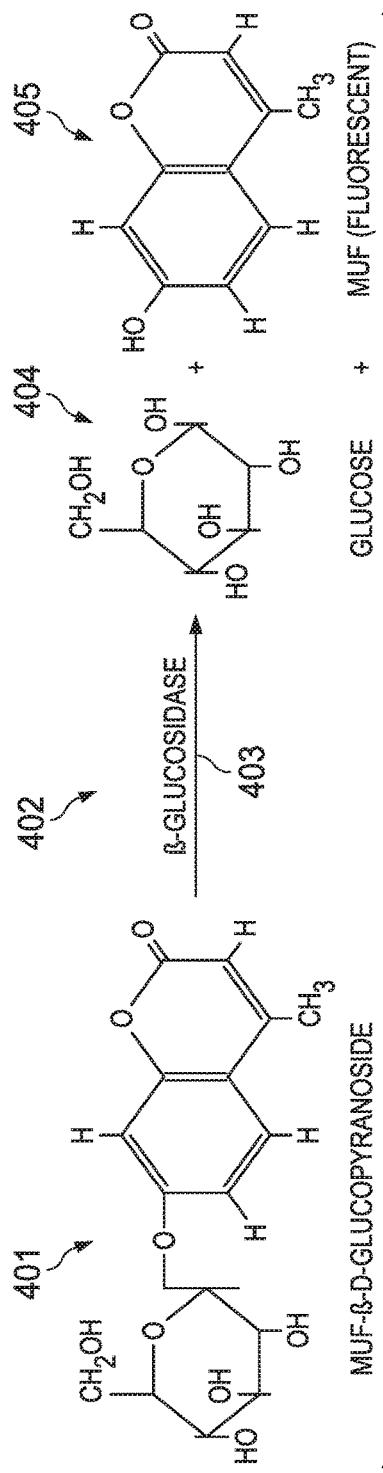
FIG. 4A is a schematic of fluorogen-substrate enzymatic cleavage.
Figure 4B:
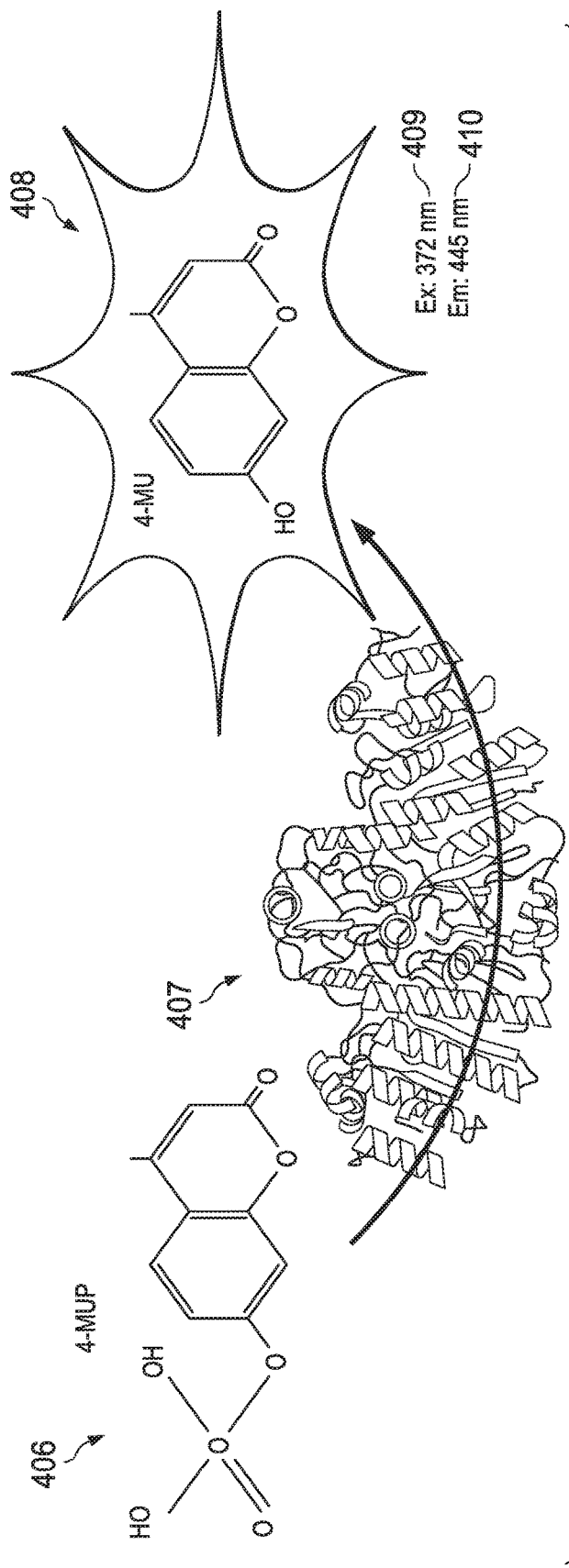
FIG. 4B is a schematic of extracellular enzyme activity (EEA) using fluorescence.

FIG. 4A is a schematic of fluorogen-substrate enzymatic cleavage. In the example, the hydrolysis reaction 403 of the fluorogen-substrate 401 (MUF-β-D-glucopyranoside) by the hydrolytic enzyme 402 (n-glucosidase) results in formation of a glucose product 404 and a fluorescent product (MUF) 405. In FIG. 4B, another cleavage example shows the fluorogen-substrate 4-MUP (406) is acted on by the ALP enzyme (407) to produce the fluorescent product 4-MU (408). Excitation wavelengths (409) and emission wavelengths (410) are measured and the fluorescence readings can be correlated to the level of extracellular enzyme in the assayed environment.

4-methylumbelliferone (MUF) is the most widely used fluorogen molecule in F-S for bacterial enzyme applications. Along with MUF, three other fluorogens, 7-amino-4-methylcoumarin (AMC), p-nitroanilide (pNA) and β-naphthylamide (β-nap) have been conjugated to unique substrates, however, these newly conjugated F-S molecules have not been fully characterized and MUF conjugates have been found to be the most suitable for the disclosed EEA assay method.

Characterization of F-S is important to selecting the best F-S for measuring bacterial populations in applied systems. Ambient factors, such as pH and temperature, have a substantial effect on three very important parameters, 1) extracellular enzyme kinetics; 2) fluorogen signal intensity; and 3) fluorogen signal stability. Enzymes catalyze reactions by reducing the activation energy required and are governed by pH and temperature sensitivities, which are hyperbolic in nature. Most importantly, the extracellular enzyme must be able to cleave the F-S efficiently. This is the prime consideration for downstream F-S selection.

Once the fluorogen is liberated by the enzymatic cleavage, fluorogen signal intensity is governed by ambient conditions. Fluorescence signal has been demonstrated to increase by a factor of 100× simply by modulating pH from 7 to pH 10, and fluorogen stability over time is effected by pH. A longer lasting signal is more favorable in industrial application. In water desalination systems, factors such as pH and temperature are dependent on characteristics of the feed water and surrounding operating conditions. Water emanating from different sources has distinct properties. Hence, an F-S appropriate for Red Sea water may not perform as well in water originating off the coast of Norway due to temperature and/or pH differences. When developing a system for measuring bacteria using the F-S system, characterization of F-S cleavage by extracellular enzymes, fluorogen signal intensity, and signal stability are reliant on localized pH and temperature parameters and must be taken into consideration.

Figure 5:
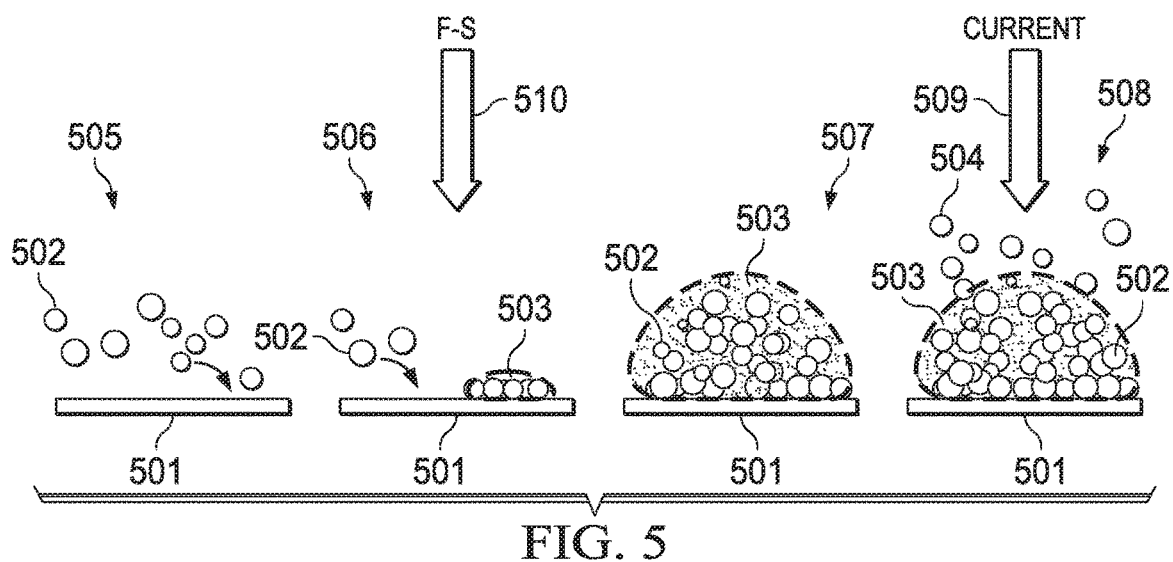
FIG. 5 is a schematic of biofouling detection in cleaning procedures.

FIG. 5 demonstrates the point that the present method is able to detect the extracellular enzymes. Shortly after the Stage 1 (505) cell adherence point, the fluorogen-substrate assay point 510 can detect the enzymes formed by the Stage 2 (506) microcolony growth. The current point 509 of detecting bacterial colonies 503 on membrane surfaces 501 is well beyond the Stage 3 (507) point of widespread colonization on the membrane 501, and is not detectable until Stage 4 (508) in the growth cycle when bacteria 502 in the colonies 503 are dispersing 504 leading to an increase in biofouling in other locations, and typically by this point, membranes have already experienced a significant decrease in function.

In a second embodiment, an at-line membrane fouling sensor system is disclosed herein that utilizes a fluorogen-substrate based Extracellular Enzyme Activity (EEA) assay for early detection and quantification of bacterial activity based on the presence of bacterial extracellular enzymes present in the fluid medium around the membrane. As described herein, the sensor is useful for detecting and quantifying membrane biofouling used at-line adjacent to a water filtration system, but the sensor can be used in other applications where biofouling may occur. The sensor described herein is particularly advantageous when used in water desalination systems. Reverse osmosis membrane and forward osmosis membrane filtration systems are the most efficient systems for water desalination, but the sensor herein may be used with other types of membrane filtration systems that are subject to biofouling. The present invention can also be proactive using an aqueous medium after calibration.

Figure 6A:
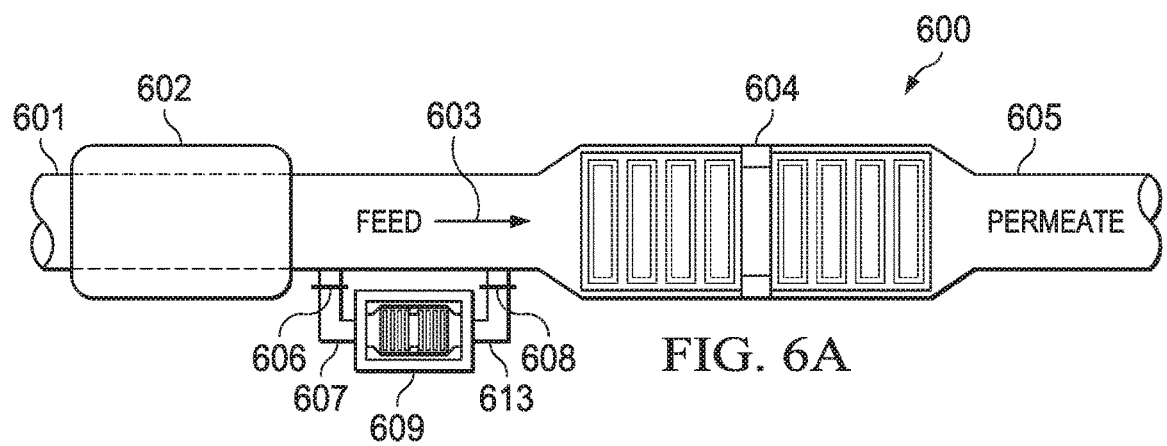
FIG. 6A is a schematic of a filtration system.

FIG. 6A is a schematic of a membrane filtration system 600 showing the introduction of the disclosed at-line sensor 609 into the filtration system. In the example, the at-line sensor 609 is situated adjacent the feed solution stream 603, after the pretreatment unit 602, and prior to the main filtration system. In use, water enters the pretreatment unit 602 via water inlet 601 and the feed solution stream 603 flows the water into the main filtration unit 604 for desalination and the desalinated water, or permeate, exits via permeate outlet 605. The sensor inlet valve 606 and sensor outlet valve 608 are open and the feed solution stream flows through the sensor 609 along the inlet conduit 607 and out of the sensor along outlet conduit 613 passing back to the main feed solution stream 603, thus allowing the sensor membrane to encounter the same water conditions as the main filtration system.

Figure 6B:
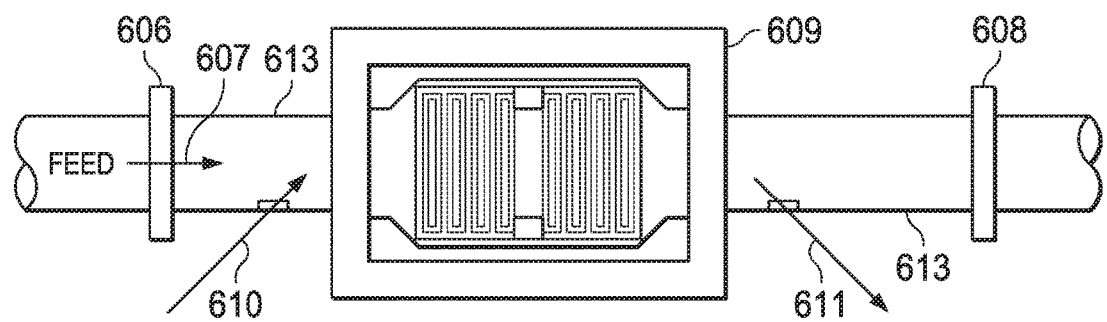
FIG. 6B is a schematic of flow through an at-line filter in the filtration system of FIG. 6A.

FIG. 6B shows the functional design of the at-line sensor for monitoring membrane health. EEA measurements obtained from the F-S assay system are used to measure bacterial dynamics on membranes associated with seawater desalination systems within a closed system. To achieve this closed system function, the sensor 609 is a modified flow-cell, having features of the membrane filtration system 600 module and functions at-line of the feed stream 603 entering a desalination module from the pretreatment unit 602. The sensor 609 is compact and simulates conditions within the larger desalination membrane filtration unit 604, has similar hydrodynamic behavior and would be subject to the same biofouling as the main membrane unit 604.

Figure 6C:
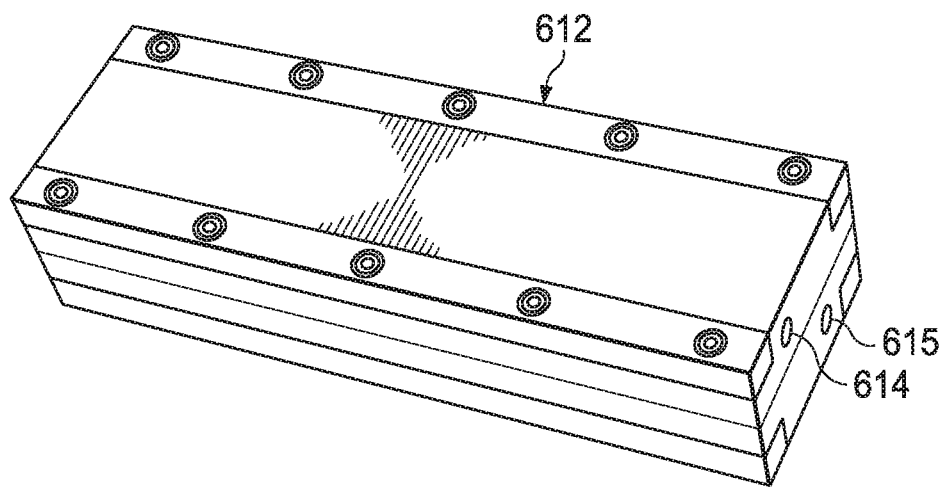
FIG. 6C is an example of an at-line filter for use in the filtration system of FIG. 6A.

A number of studies have been conducted to validate a simulator as representative of operating conditions found in desalination systems. The sensor may optionally be opaque overall or optionally may have a transparent portion for direct observation of the membrane. An example sensor 612 is depicted in FIG. 6C. Flow pathways (614, 615) through the sensor (612) direct the feed stream solution across the sensor membrane. In present invention system, the feed flow is linear, with an adjustable flow range from 1.5-20 liters per hour. Due to the construction, the sensor can be operated at temperature from 0-70° C. The primary aim of the present invention system is to measure biofouling growth over time. A host of membranes can be tested, but most experiments rely on a single nanofiltration (NF) membrane in the presence of a feed channel spacer. This configuration uses the basic components of a desalination membrane module.

Following the schematic in FIG. 6B, the inlet valve 606 and outlet valve 608 of the at-line sensor 609 can be closed at set time points for gauging bacterial EEA without interrupting operation of the main membrane unit 604. Once valves 606 and 609 are closed, the selected Fluorogen-Substrate can be injected into the at-line sensor 609 through the injection port 610. Following incubation, aliquots are removed via the sample (flush) port 611 and read externally by a fluorometer in 96 well plate. Alternatively, liberated fluorogens from the EEA assay can be detected using an online fluorometer. After testing, which typically lasts no more than 30 minutes, the sensor 609 is flushed of residual F-S and byproducts by flushing materials in the sensor 609 out through the sample (flush)port 611. After flushing is completed, the inlet valve 606 and outlet valve 608 are reopened and the feed stream passes through inlet conduit 607 to the sensor 609 and flows via outlet conduit 613 to the main feed solution stream (603) as before. At each time point, 30 minutes of Fluorogen-Substrate incubation was selected as a balance between realistic sampling time and resulting signal strength; however the dwell time of the Fluorogen-Substrate in the sensor can range from 1 minute to 60 minutes as needed for the testing parameters. Increasing the incubation time should result in increased signal strength as more fluorogen liberation can occur.

The at-line sensor 609, which is positioned adjacent the main membrane unit 604 and not in the main feed stream flow, is open to manipulations that are not possible for on-line systems. Conditions such as pH and temperature can be adjusted during the measurement phase. For example, adjusting pH can be accomplished during testing by injecting the F-S in either an alkaline or acidic solution, depending on the parameters required for the specific fluorogen-substrate being used. Similarly, enclosing the sensor inside a temperature-controlled cabinet can control temperature to levels that are not possible with the main module. Optimal temperature and pH differ depending on the specific combination of fluorogen-substrate and matrix (e.g., seawater or drinking water) being processed in the membrane filtration system, and the disclosed system is able to accommodate means to achieve the optimal temperature and pH for the assay.

Baseline monitoring of an at-line sensor using fluorogen-substrates have been tested. Lab-scale simulators with the capability to be locked and analyzed using EEA measurements were used to assess the assay system. A locked state is required to control the reaction products generated post-enzymatic activity. EEA measurements were taken longitudinally at the inlet (feed), concentrate side, and the permeate side. Fluorogen and substrate were followed to determine post cleavage fate. All measurements were taken in addition to ATP and operating parameter measurements, such as pressure drop. A schematic of the process is shown in FIG. 6B.

Feed water consisted of incubated seawater inoculum, which was allowed to colonize the simulator membrane and F-S measurements were determined. Longitudinal studies paired to current state of the art were used to assess biofouling risk. EEA measurements, paired with operational measurements, were used to develop a biofouling risk index for guiding cleaning protocols, particularly relating to timing cleaning before significant reductions in membrane function occur.

Various techniques have been developed in parallel to monitor the real-time state of water filtration modules. Technological advances in detecting fluorescence, along with the cost-effective availability of commercial F-S libraries have increased the feasibility and reliability of the F-S EEA assay system. The disclosed at-line sensor is a device capable of being attached upstream in a membrane filtration system and the at-line nature of the module acts similarly to a "canary in a coal mine" warning of declining conditions in the membrane. Left unchecked, biofouling of the membrane leads to increased costs and decreased potable water. The disclosed method and sensor provide an early warning for detecting biofouling allowing corrective cleaning measures to be taken before the membrane function decreases to an unacceptable level. Measuring enzymatic activity by fluorogen-substrates cleavage in an at-line sensor is therefore a tool to monitor membrane health for guiding anti-biofouling practices.

An assay for measuring Extracellular Enzyme-based activity for use in a biofouling sensor for early detection of biofouling was developed. In vitro extracellular enzyme activity assays for a seawater and drinking water matrices were used for High-Throughput Screening (HTS) on a library of fluorogen-substrate compounds. Down-selected fluorogen-substrates were characterized based on the effect of pH and temperature. The assay is used in conjunction with the at-line sensor to monitor membrane health. The at-line sensor is a tool to predict biofouling using fluorescent measurements of EEA by monitoring precursors of biofouling bacterial activity. The EEA fluorogen-substrate assay is used with the at-line biofouling sensor and monitors the membrane at-line, using non-invasive, rapid and sensitive techniques essential to guiding anti-biofouling practices of membrane based filtration systems, particularly in saline environments.

Materials and Methods:

The process steps for developing the assay and sensor are described herein. Optimal conditions, such as preferred temperature and pH, were determined for specific combinations of fluorogen-substrates and matrices.

Bacteria utilize ubiquitous extracellular enzymes involved in the conversion of organic molecules to assimilable organic molecules. Since each cell releases a large number of extracellular enzymes into the surrounding matrix, extracellular enzymes measurements are an amplified signal for determining bacterial quantity. Extracellular enzymes can cleave fluorogen-substrate compounds to release a strong fluorescent signal. The catalytic activity of extracellular enzymes in a seawater matrix was measured to determine sensitivity of the cleavage. Catalytic activity depends on the affinity to the substrate-fluorogen introduced. Extracellular enzyme cleavage of fluorogen-substrate compounds occurs via enzyme-substrate kinetics that are determined by pH and temperature.

Bacterial extracellular activity was used to predict the initiation of biofilm formation. Since bacteria are single cell organisms that multiply in appropriate conditions, it is possible for persister cells to initiate biofilm formation. Measuring the extracellular enzyme activity in a closed system longitudinally, allows tracking of bacterial biofilm development over time.

Figure 7:
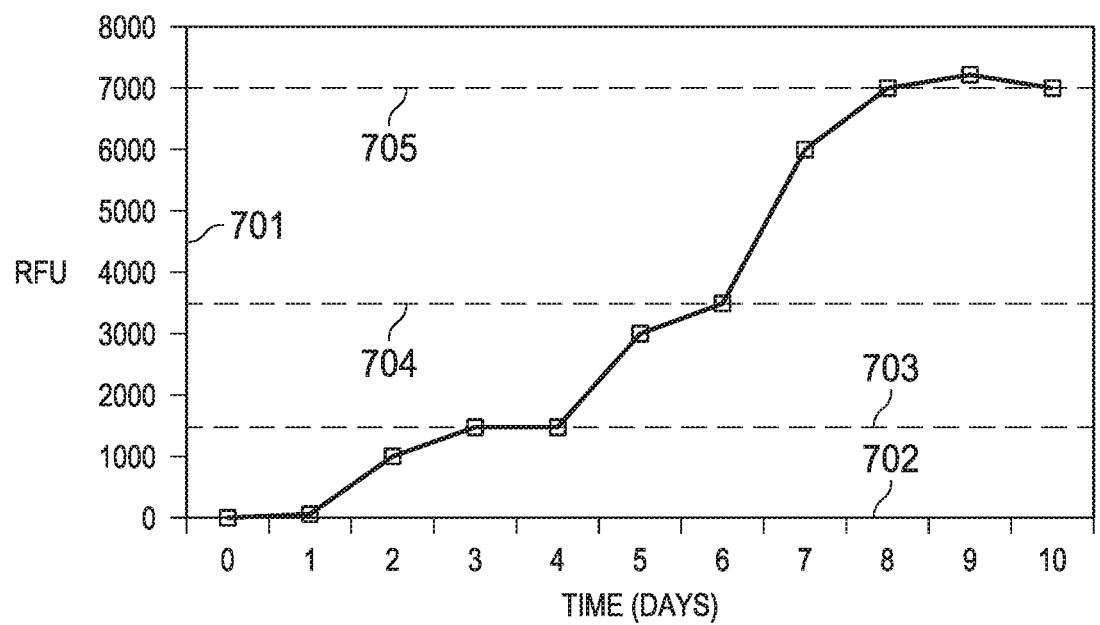
FIG. 7 is a graph showing biofouling risk index.

FIG. 7 is a graph 700 of the biofouling risk index based on the bacterial extracellular enzyme activity over time. A membrane fouling simulator was used as an at-line "sensor" to represent a membrane filtration system. Monitoring the extracellular enzyme activity and common operational parameters involved in biofouling longitudinally in the simulator were used to develop a biofouling risk index. Extracellular enzymes are composed of two major groups, ecto and exo, which are designated by cellular localization. Using EEA measurements in a sensor, ecto-enzymes will exhibit the least amount of signal interference in environmental conditions because of attachment to cell membrane. Meanwhile, exo-enzymes will exhibit high background signal noise as exo-enzymes travel through upstream filtration units unattached to bacterial cells.

During the simulator testing, fluorescence measurements enabled tracking of bacterial colonization on the membrane surface and the bacterial colonization signal was calibrated to develop a Biofouling Risk Index (BRI) seen in FIG. 7. Samples from the membrane simulator were assayed using the fluorogen-based EEA assay method over a period of 10 days (702) and Relative Fluorescence Units (701) were measured. A normal fluorescence level 703, indicated by RFU of 2000 or less, was measured over the first four days. An increase to 3500 RFU occurred between the fourth and fifth days indicating that cleaning should be initiated (704). A rapid increase in RFU occurred over days six through ten with RFU of 7000 occurring for days 8-10 indicating that the system was biofouled 705. This index can be used to guide currently arbitrary cleaning protocols, thereby mitigating impact of bacterial biofouling, in industrial processes, specifically in the desalination of seawater.

FIGS. 8A and 8B show the extent of biofouling measured over 84 hours corroborated by images of bacterial adherence on the simulator membrane at selected time-points. The graph 800 shows the extracellular enzyme activity (EEA) signal (803) measured by the cleavage of fluorogen MUF increases as bacteria accumulate on the membrane. RFU (801) increased steadily as the hours passed (802). Optical Coherence Tomography images (807-811) captured from the simulator membrane depict a correlation between the increase EEA signal 803 shown on the graph and the increase of visible bacteria on the membrane over the same time.

Fluorogen-Substrate Preparation: Fluorogen-substrates for bacterial enzymes were acquired from Sigma-Aldrich (MO, USA) as lyophilized powder. Chemicals were weighed and reconstituted using sterile water to desired stock concentration. Standards were stored at 4° C. and fluorogenic-substrates were stored at −20° C.

TABLE 2

Fluorogen substrates with corresponding standards (from Sigma Chemical)

| Compound | Cat no. | Molecular Weight | Fluorogen |
| --- | --- | --- | --- |
| 4-methylumbelliferone | M1508 | 198.15 | Standard |
| Methylumbelliferyl(MUF)-phosphate | M8883 | 256.15 | 4-methylumbelliferone |
| MUF-N-acetyl-β-D-glucosaminide | M2133 | 379.36 | 4-methylumbelliferone |
| MUF-β-D-glycopyranoside | M3633 | 338.31 | 4-methylumbelliferone |
| MUF-heptanoate | M2514 | 288.34 | 4-methylumbelliferone |
| 7-amino-4-methylcoumarin | A9891 | 175.18 | Standard |
| L-Leucine-7-amido-4-methylcoumarin | L2145 | 324.80 | 7-amino-4-methylcoumarin |
| β-naphtylamine | N8381 | 143.19 | Standard |
| L-Leucine-β-naphtylamide hydrochloride | L0376 | 292.80 | β-naphtylamide |

Figure 9:
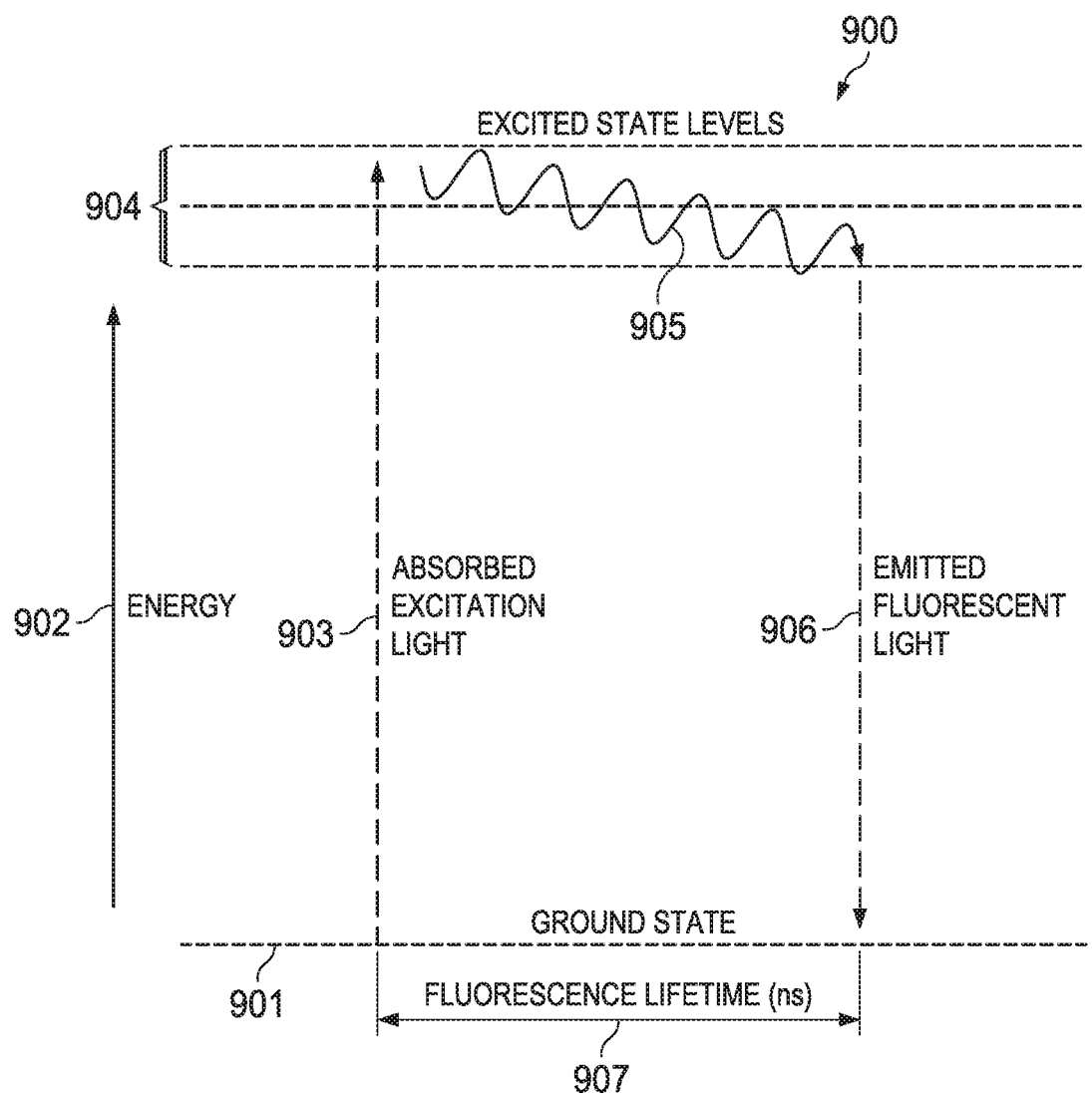
FIG. 9 is a Jablonski diagram outlining the process of excitation and subsequent emission during fluorescence.

Stability of Fluorogen signal—As seen in the FIG. 9 Jablonski diagram 900, fluorescence is a function of electron excitation 903 from ground state 901 to a higher energy 902 level to reach an excited state level 904. After a certain period of time, an electron will de-excite 905 returning to its normal state, emitting energy 906 at a specific wavelength in the process over the fluorescence lifetime 907. The energy emitted as fluorescence can be reliably measured to quantify the activity in the EEA assay.

Conditions for the EEA assay, such as fluorescence signal related to concentration of fluorogen-substrate, fluorescence signals in differing matrices, temperature dependence and pH dependence, were characterized in order to determine the optimal performance conditions for the assay to produce consistent results. FIGS. 10-14 indicate a summary portion of the results obtained for these conditions.

FIG. 10 is a graph of varying concentrations of one fluorogen-substrate assayed in the same matrix (seawater) under the same operating conditions. The graphs shows the fluorogen substrate signal for standardized Red Sea water inoculum titrated and measured for EEA using MUF-phosphate (0.5 µM) showing Relative Fluorescence Units 1001 over Time (minutes) 1002 indicating fluorescence level over the various titrations. At 100% (1003), the signal was 25000 RFU at 90 minutes with no signal from the no MUF-phosphate control 1010. The intervening signals 1004-1009 showed decreasing signal levels as MUF-phosphate concentration decreased. Linear signals were obtained for 3.0% (1008) and 1.6% (1009).

Figures 11A, 11B:
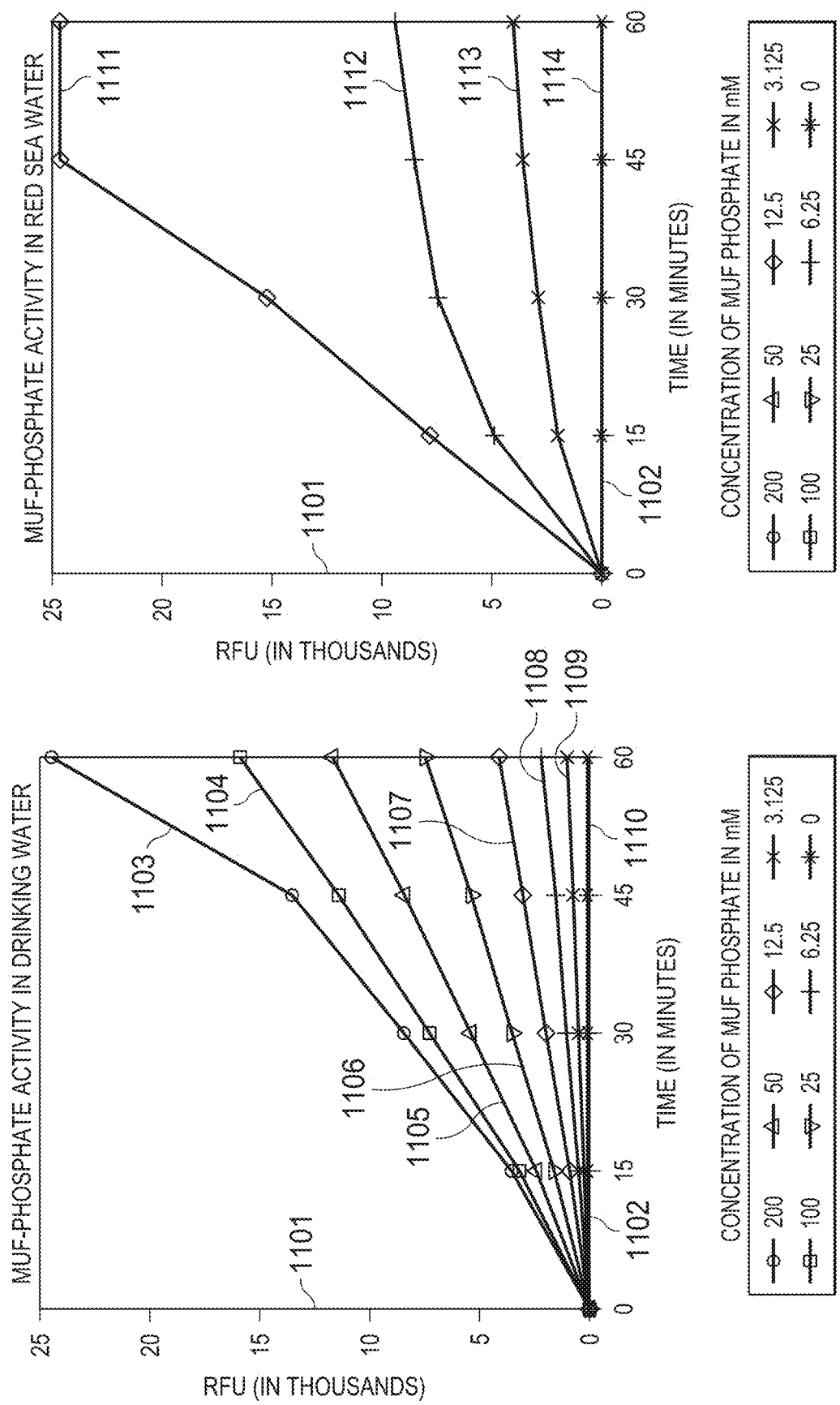
FIGS. 11A and 11B are graphs of MUF-phosphate activity in drinking water and seawater.

FIGS. 11A and 11B are graphs demonstrating the matrix dependence for the fluorescence signal. MUF-phosphate activity was tested under similar conditions at varying concentrations for two matrices—drinking water and seawater. In 11A, Relative Fluorescence Units (1101) were measured over time in minutes (1102) with drinking water alone (1010) and for varying concentrations of MUF-phosphate (1104-1109) in a drinking water matrix. In 11B, Relative Fluorescence Units (1101) were measured over time in minutes (1102) with seawater alone (1011) and for various concentrations of MUF-phosphate (1111-1113) in a seawater matrix. The signals for the seawater matrix at MUF-phosphate concentrations of 12.5 µM, 6.25 µM, and 3.125 µM (111-1113) were much higher than for the same concentrations for the drinking water matrix (1107-1109).

FIGS. 12A and 12B are graphs showing temperature dependence of signals for two fluorogen-substrates. MUF-N-acetyl-β-D-glucosaminide and MUF-phosphate were tested under the same conditions at 25° C., 35° C., 45° C. and 55° C. Relative Fluorescence Units (1201) were measured over time (1202) for both substrates. The fluorescence signal was similar for both substrates at 25° C. (1206, 1210). As temperature increased, MUF-phosphate showed a corresponding increase in signal at 35° C., 45° C. and 55° C. (1207-1209). MUF-N-acetyl-β-D-glucosaminide, also showed an increase in the signal at 35° C. and 45° C. (1203-1204), however, the signal at 55° C. (1205) was less than either of the signals at 35° C. and 45° C.

FIG. 13 is a graph showing the effect of pH on fluorescence intensity. Relative Fluorescence Units (1301) were measured over a pH range from pH 7-pH 10 (1302). The fluorescence signal 1303 for the MUF standard increases as the pH in the solution increases.

FIG. 14 is a bar graph of the effect of pH on extracellular enzyme cleavage of two fluorogen-substrates. The Relative Reaction Velocity (1401) is compared for fluorogen-substrate cleavage of MUF-phosphate and MUF-N-acetyl-β-D-glucosaminide by extracellular enzymes over a pH range from pH 7-pH 10 (1402). Reaction velocity increased for MUF-phosphate from pH 7 (1403) to pH 8 (1405), peaking at pH 9 (1407), then decreasing at pH 10 (1409). For MUF-N-acetyl-β-D-glucosaminide, the Reaction velocity also increased from pH 7 (1404) peaking at pH 8 (1406), then decreased at pH9 (1408) and pH10 (1410). These results from FIGS. 13 and 14 indicate that not only are fluorescence intensity and reaction rates affected by pH, but the effect is also substrate-dependent.

Extracellular Enzyme Activity Assay development using Fluorogen-Substrates—The EEA Assay method was used determine detection using F-S for titrated bacterial concentrations.

Figure 15:
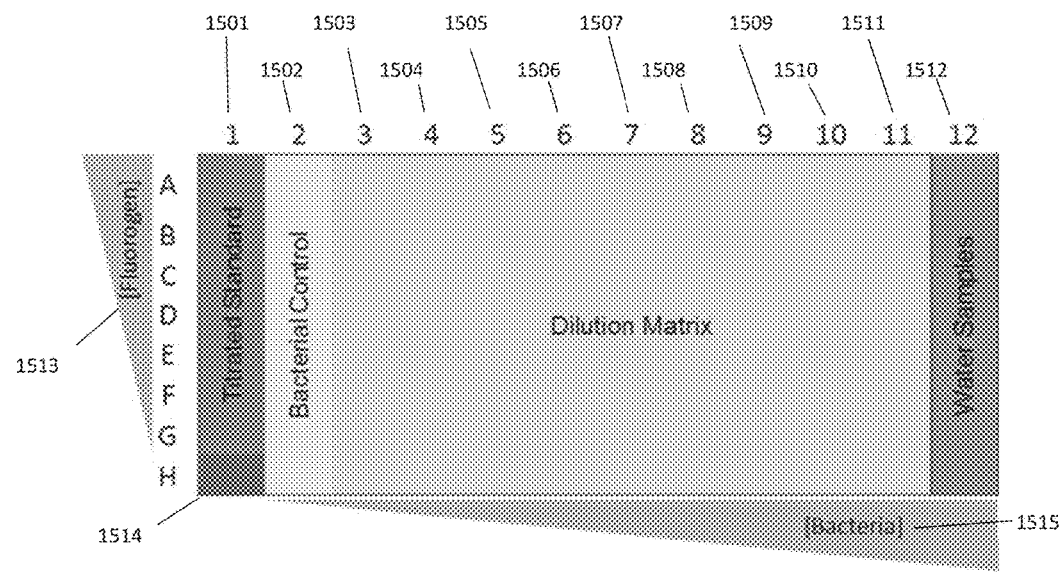
FIG. 15 is a graph of 96 well plate setup to assess sensitivity of fluorogen-substrate in titrated water samples.

Early assays with titrations of bacteria and constant F-S concentrations were setup as per FIG. 15 in a 96-well black flat-bottom micro-titer plate. Briefly, 100 µl, of appropriate dilution matrix was added to all wells of columns 2-11 (1502-1511). Furthermore, 100 µL of dilution matrix was added to wells B-H of column 1 (1501). Water sample inoculum was added (200 µL/well) in column 12 (1512). Using a multi-channel pipette and aseptic technique, 100 µL from the contents of column 12 was serially diluted two-fold to column 3 and the final 100 µL was discarded. Column 2 (1502) is the negative control having dilution matrix with no bacteria. Column 1(1501) is used for fluorogen standard dilution. 200 µL of fluorogen standard was added to well A1. Two-fold dilutions of the fluorogen standard were made by transferring 100 µL from A1 to B1, B1 to C1; repeating until G1 and discarding the final 100 µL. Well H1 (1514) is the control for background fluorescence signal noise.

MUM Before each plate is read, 50 µL of fluorogenic substrate (saturating amount) was added from a reservoir using a multichannel pipette to all wells of columns 2-12 (1502-1511). In the general procedure, fluorogen-substrate concentration (1513) deceases in the rows from top to bottom and bacterial load increases (1515) in the columns from left to right. Fluorescence measurement using the correct excitation and emission wavelengths for the fluorogen selected were begun immediately following addition of F-S. Generally, 350 nm excitation and 465 nm emission has been used with the above mentioned fluorogenic substrates.

Drinking and seawater samples—Water samples were collected from the Water Desalination & Reuse Center inlets. Seawater source is unfiltered Red Sea water originating in the area near Thuwal, Saudi Arabia. Drinking water was filtered through carbon filters to remove residual chlorine. Samples were collected in sterile 50 mL conical tubes and used same day.

Preparation of inactivated matrix as dilution matrix—Proper dilution matrix with the same characteristics of the test water is important to control testing by standardizing matrices. A dilution matrix was prepared by heating drinking water or seawater to 90° C. for 20 minutes to inactivate proteins and enzymes, followed by cooling to room temperature in a water bath. The room temperature matrix is filtered through a 0.22 µM filter unit to remove microbes and is referred to as Drinking Water$_{BF}$ or Seawater$_{BF}$. An additional matrix is prepared without inactivation, which is filtered through a 0.22 µM filter unit to remove microbes and referred to as either Drinking water$_F$ or Seawater$_F$. All dilution matrices are stored at 4° C. Before use, the dilution matrix is acclimated to room temperature in a water bath. Side by side comparison indicate no significant difference between boiled & filtered vs. filtered only, hence all subsequent experiments use the boiled & filtered dilution matrix.

Preparation of Yeast Extract—Yeast Extract (YE) in a powdered form was obtained from Sigma-Aldrich and a 100× solution was prepared in water and filter sterilized using a 0.22 µM filter unit.

Absorbance and Fluorescence measurements—A spectrophotometer, namely the SpectraMax M5e (Molecular Devices, USA) was used in all experiments to measure absorbance and fluorescence. Measuring sample absorbance at 600 nm (Abs$_{600}$) is commonly used to quantify bacterial growth. Absorbance was measured using a 96-well clear flat-bottom plate. Fluorescence was measured at excitation 355 nm and emission at 465 nm unless otherwise stated and reported as Relative Fluorescence Units (RFU). All fluorescence measurements were performed in opaque 96-well black micro titer plates. Kinetic measurements, data collected at set intervals over a period of time, were used to measure each well temporally.

Graphing software—Spectrophotometer data were recorded using SoftMax Pro Data Acquisition Software Version 5.4 (Molecular Devices, USA). Graphs were generated using the software when applicable. A custom Tensor Program (ARK Computers, NY, USA) was used to export kinetic fluorescence data acquired by the SpectraMax M5e. Graphs were generated using GraphPad Prism Version 5.0 (GraphPad Software, Inc, USA).

Flow Cytometry—Flow Cytometer Measurement (FCM) is a reliable method to estimate bacterial cell counts when performed by a trained flow cytometrist. Samples are first labeled with fluorescent dyes, which are then counted based on signal properties as the sample passes through an array of fluorescence detectors. Here, FCM has been used to estimate the total bacterial population of water samples using the Accuri C6 Flow Cytometer (BD Bioscience, USA) instrument to determine approximate bacterial counts.

Quality Control protocol for the Accuri C6 Flow Cytometer—After power-on, Quality Control (QC) must be run daily before measuring samples. The QC was adapted from the manufacturer's protocol which incorporates a cleaning cycle using detergent, soap and subsequent washes with sterile water. Lastly, a calibration check using a standard reference bead mixture is performed. Spherotech 8-peak Validation beads for FL1-FL3 (BD Accuri, cat. no. 653144) is prepared by adding 3 drops to 10 mL of sterile MilliQ water and vortexed for 15 seconds. FCM of the validation mixture should measure 8000 events/50 µL. Internal calibration of the instrument is ensured in this procedure.

Sample labeling protocol—appropriate volumes of water sample were collected after incubation and serially diluted two-fold into the appropriate dilution matrix. At time of analysis, the sample tubes are acclimated to 35° C. in a water bath for 10 minutes. After acclimation, SYBER Green 1 (Life technologies, working stock 100×) was added 1:100 to each sample tube and further incubated at 35° C. in a water bath for 10 minutes. Labeled samples were transferred to individual wells of a 96-well flat bottom micro titer plate for FCM. Plates are setup for sample reads using the following settings; Slow speed and 50.0 µL total volume read.

Bacterial capacity in drinking and seawater—Drinking water and seawater were characterized to establish standardized inoculum for EEA assay development. Conductivity, pH, and Total Dissolved Solids (TDS) were measured.

Figure 16A:
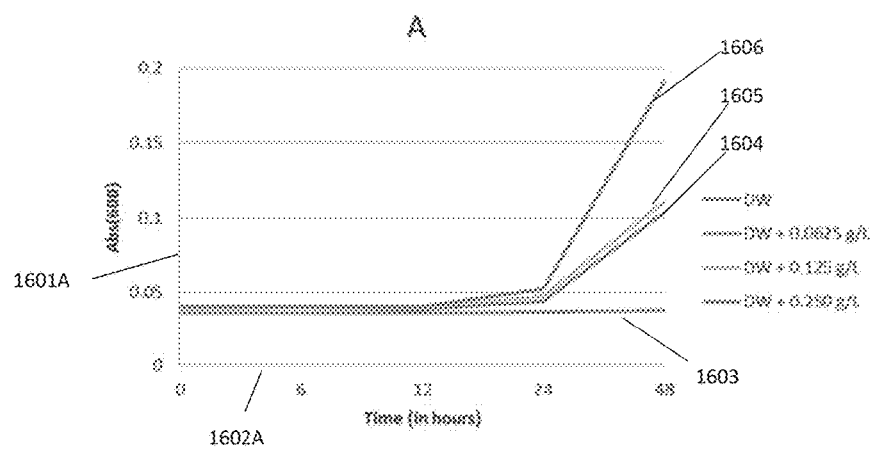
FIGS. 16A and 16B are graphs of absorbance at 600 nm for drinking water and seawater with yeast extract.
Figure 16B:
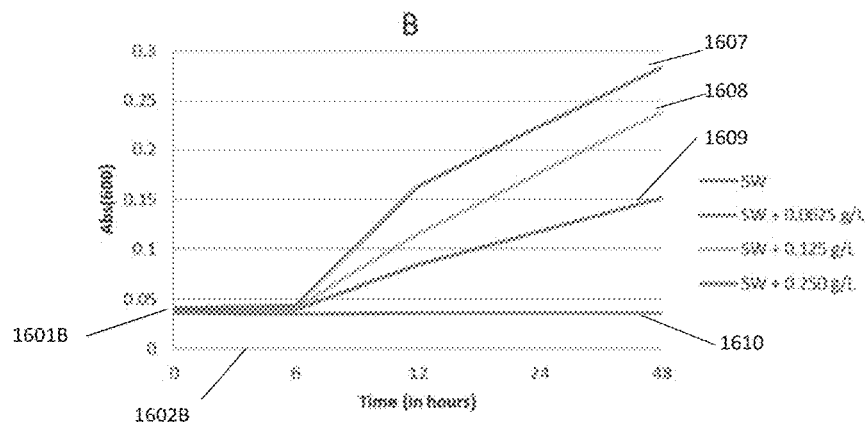

Water samples supplemented with Yeast Extract—Drinking and seawater samples supplemented with YE (0-0.5 g/L) were incubated to characterize bacterial growth at 37° C. over a period of 48 hours. Conductivity, pH, and TDS were recorded for each sample after 48 hours of incubation at 37° C. (Table 3). Absorbance at 600 nm was measured every 6 hours and graphed over time. The graph in FIGS. 16A and 16B show absorbance (1601) over time in hours (1602) with results for Drinking water in FIG. 16A and seawater in FIG. 16B. Absorbance in the Drinking water samples over the concentration ranges (1603-1605) were generally in the range of the no-extract control (1606) over the first 12 hours with increases becoming evident from 12-24 hours and showing a marked increase from 24-48 hours. Absorbance in the seawater samples over the concentration ranges (1607-1609) were generally in the range of the no-extract control (1610) over the first 6 hours with marked increases becoming evident from 6-48 hours. These results indicate the variability of absorbance in differing water types previously seen in non-supplemented matrices is still evident when the yeast extract is added to the solution.

TABLE 3

Characterization of Drinking and Seawater after 48 hours with varying concentrations of yeast extract

| DW after 48 hours with varying YE | | Filtered | +Bacteria |
|---|---|---|---|
| Drinking Water (DW) | pH | 7.7 | 7.7 |
| | Conductivity (uS) | 1200 | 1200 |
| | TDS (ppm) | 600 | 600 |
| DW + 0.125 g/L YE | pH | 7.1 | 6.9 |
| | Conductivity (uS) | 1200 | 1600 |
| | TDS (ppm) | 600 | 833 |
| DW + 0.25 g/L YE | pH | 6.9 | 6.8 |
| | Conductivity (uS) | 600 | 2000 |
| | TDS (ppm) | 400 | 1000 |
| DW + 0.50 g/L YE | pH | 6.7 | 6.7 |
| | Conductivity (uS) | 2500 | 3000 |
| | TDS (ppm) | 1400 | 1500 |
| SW after 48 hours with varying YE | | Filtered | +Bacteria |
| Seawater (SW) | pH | 7.8 | 7.8 |
| | Conductivity (mS) | 45 | 45.6 |
| | TDS (ppt) | 23 | 23 |
| SW + 0.125 g/L YE | pH | 7.0 | 6.6 |
| | Conductivity (mS) | 46 | 61 |
| | TDS (ppt) | 29 | 29 |
| SW + 0.25 g/L YE | pH | 7.0 | 6.5 |
| | Conductivity (mS) | 90 | 96 |
| | TDS (ppt) | 45 | 43 |
| SW + 0.50 g/L YE | pH | 6.6 | 6.4 |
| | Conductivity (mS) | 90 | 90 |
| | TDS (ppt) | 45 | 47 |

Characterization of the starting inoculum was one of the first steps in developing an assay suitable for high throughput screening. Drinking water and seawater collected from inlets at Thuwal, Saudi Arabia were tested at various incubation times and with growth-promoting supplements. These samples were characterized using standard techniques and bacterial counts were determined. Historically, the gold standard for bacterial quantification has been to culture bacteria in growth media and report as Colony Forming Units/volume (CFU/volume). Well-known issues surrounding culture of environmental samples have opened the door for measurements using Flow Cytometry. FCM was performed on samples and it was determined that $Abs_{(600)}$ of 0.10-0.15 correlated to $6.0 \times 10^7$ bacteria per mL. Drinking water and seawater supplemented with Yeast Extract, 0.250 g/L and 0.063 g/L respectively, when incubated at 37° C. for 24 hours had absorbance values between 0.10-0.15. These conditions were standardized for all future experiments.

Fluorogenic signal is affected by matrix conditions. Signal stability over time, quenching and inhibition are dependent on matrix properties. These parameters were tested for one fluorogen below.

Methylumbelliferone (MUF)—The resulting fluorogen product in all MUF-substrates cleavage in MUF. MUF signal stability was determined by titrating MUF standard fluorogen both in filtered, and boiled+filtered seawater. The resulting fluorescence signal could therefore be examined to determine fluorogen stability and potential signal inhibitors (e.g. quenching compounds) found in the matrix.

Figure 17:
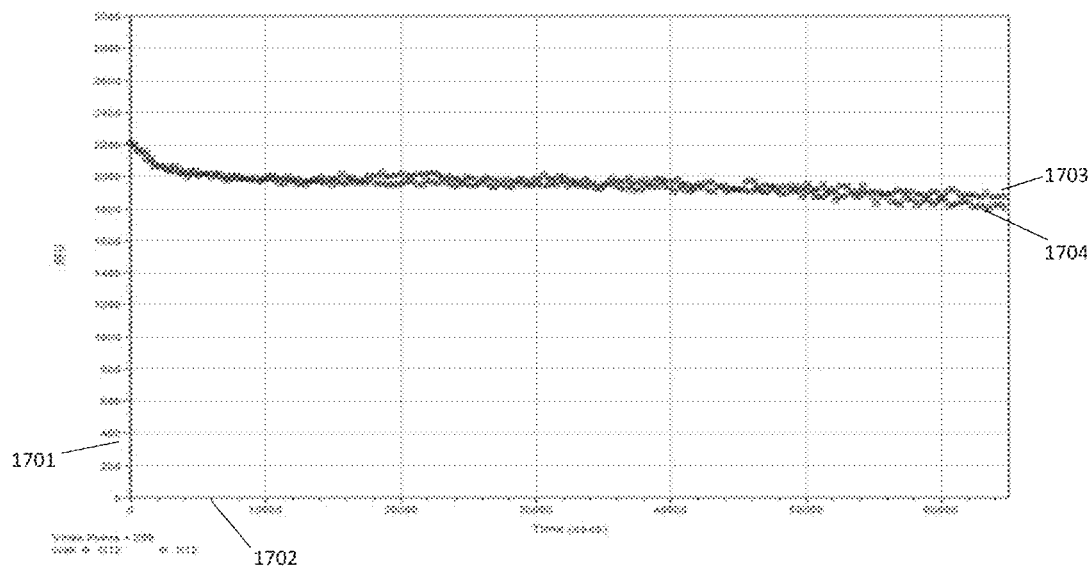
FIG. 17 is a graph of fluorescence in filtered water and filtered and boiled water.

As seen in FIG. 17, the MUF fluorescence signal remained stable with no significant decrease in RFU (1701) signal strength over a period of 18 hours (1702) of fluorescence readings. In addition, there were no significant differences between dilution matrix that was boiled and filtered (1704) as compared to filtered matrix only (1703), which points to the lack of inhibitory matrix effect.

Figure 18:
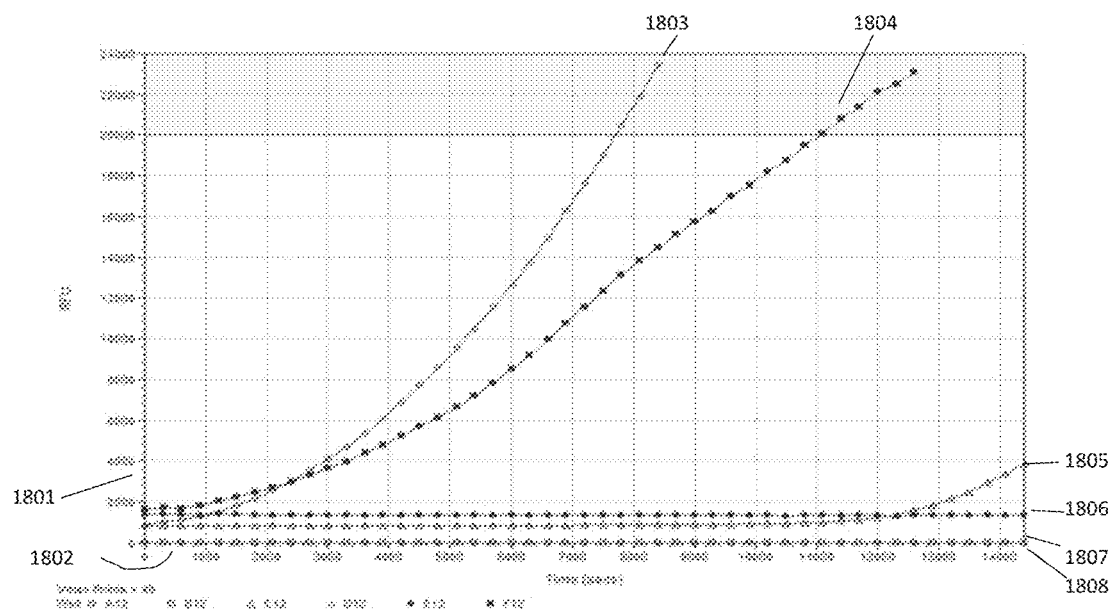
FIG. 18 is a graph of Seawater (SW) supplemented with Yeast Extract (YE) (0-2 g/L) incubated at Room Temperature (RT) or 37° C. for 12 hours and assayed for 4 hours using MUF-phosphate (250 µM final)
Figure 19:
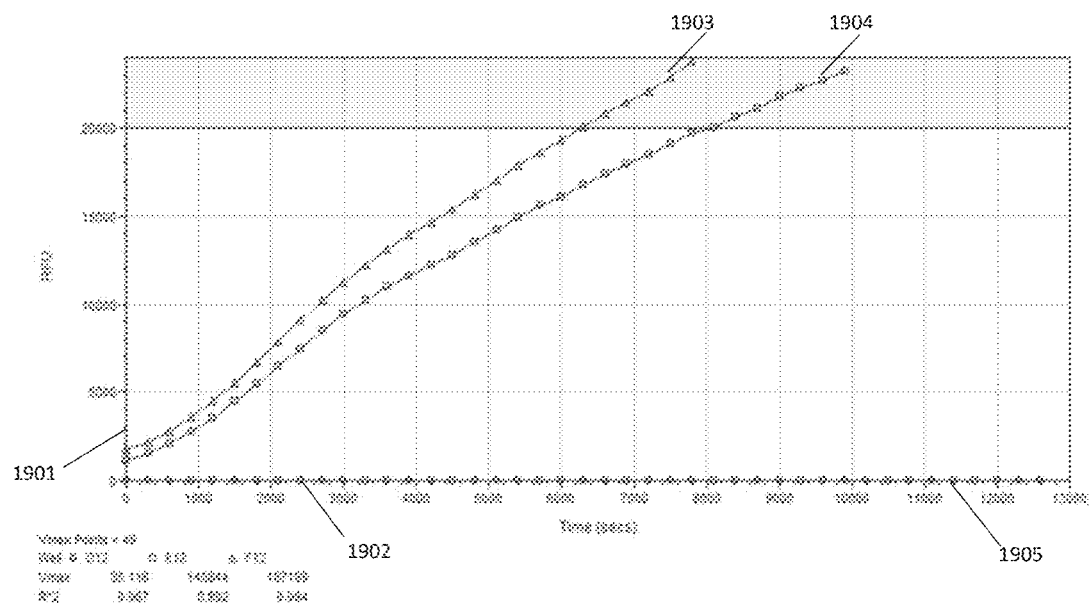
FIG. 19 is a graph of Seawater (SW) supplemented with Yeast Extract (YE) (0-2 g/L) incubated at 37° C. for 12 hours and assayed for 4 hours using MUF-N-acetyl-β-D-glucosaminide (100 uM)

EEA of drinking and seawater samples supplemented with Yeast Extract measured by F-S—Seawater samples supplemented with either 1 g/L or 2 g/L of YE were incubated at either room temperature or 37° C. for a period of 12 hours. These samples were tested for EEA using the 96-well fluorescence measurement protocol. In FIG. 18, the graph shows the RFU (1801) of the fluorogenic substrate MUF-phosphate (250 μM) RFU over time (1802) was higher for the both of the yeast extract samples incubated at 37° C. (1803, 1804) than for samples incubated at 25° C. room temperature (1805, 1806). Controls of seawater with no extract showed no fluorescence signal (1807, 1808). FIG. 19 shows the RFU readings (1901) for MUF-N-acetyl-β-D-glucosaminide (100 μM) over the 12 hour incubation period (1902) had similar results for the 37° C. samples with yeast extract (1903, 1904) and control sample (1905) as were seen for the MUF-phosphate. For both fluorogen-substrates, the samples with the higher 0.2 g/L concentration of yeast extract (1803, 1903) had greater fluorescence in less time than the samples with 0.1 g/L samples (1804, 1904).

Figure 20:
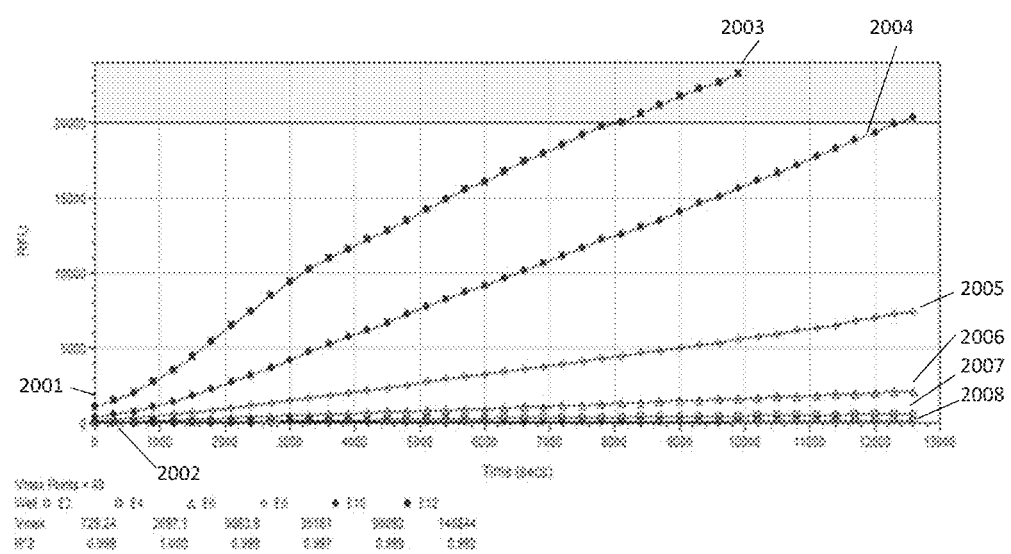
FIG. 20 is a graph of Titration of seawater sample inoculum supplemented with 1 g/L YE incubated at 37° C. for 12 hours measured for EEA activity using the F-S, MUF-N-acetyl-β-D-glucosaminide (100 µM), for 4 hours.

Seawater inoculum titrations measured by EEA—Seawater was supplemented with 1 g/L of YE incubated at 37° C. for 12 hours. The inoculum was titrated two-fold according to the procedure described above in a 96-well plate. The F-S, MUF-N-acetyl-β-D-glucosaminide (100 μM), was added to each appropriate well and the entire plate was measured kinetically for 4 hours. In FIG. 20, the results of RFU (2001) over time (2002) are shown. The controls (2007, 2008) showed no signal and the undiluted inoculum showed the highest intensity (2003). Decreasing intensity was seen as the inoculum concentration decreased to ¼, ⅛ and ¹⁄₁₆ (2004, 2005, 2006).

EEA screen of standardized bacterial inoculum using fluorogen MUF—After standardizing incubation time, temperature and YE supplement in drinking water and seawater for bacterial inoculum, multiple fluorogenic substrates were screened for rapidity, sensitivity and reproducibility. Four fluorogenic substrates were tested and the results are in the graphs in FIGS. 21-30. Versatility of the 96-well plate format also permitted fluorogenic-substrate titrations in the same assay. Titrations of the F-S can determine the least amount of F-S required while maintaining reliable and sensitive signals.

Figure 21:
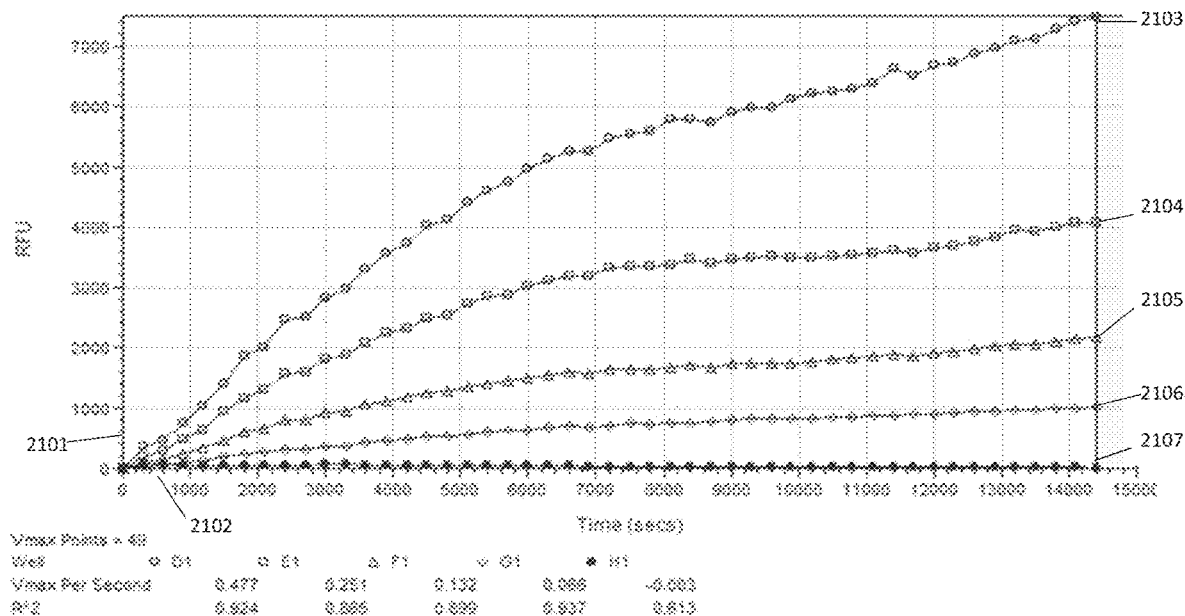
FIG. 21 is a graph of Titration of MUF standard (M1508) in a standardized drinking water inoculum.
Figure 22:
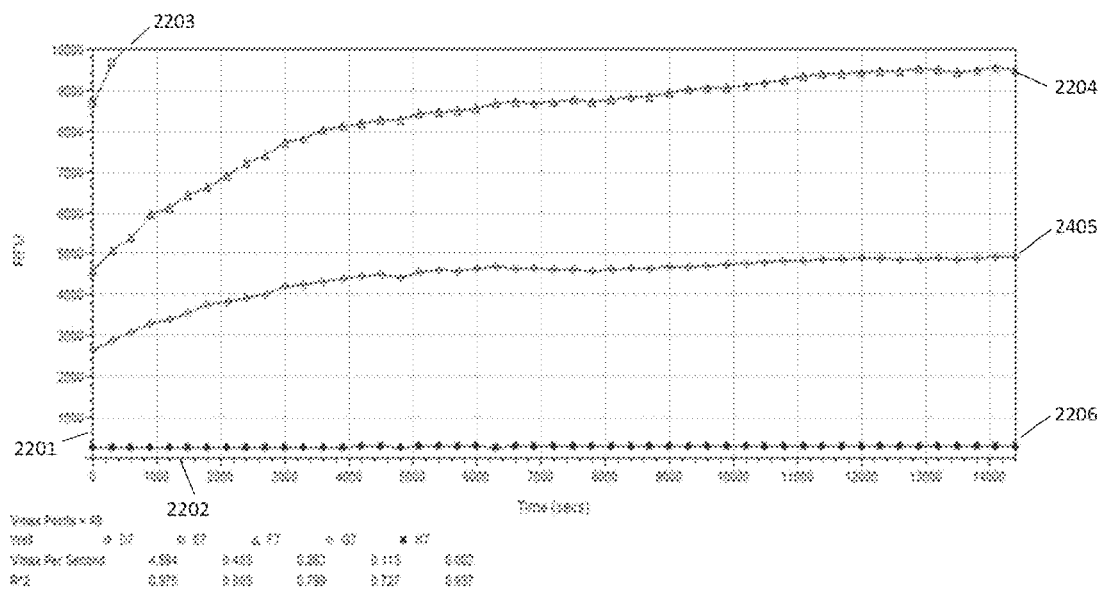
FIG. 22 is a graph of Titration of MUF standard (M1508) in a standardized seawater inoculum.

MUF standard—The FIG. 21 graph is the RFU (2101) over time (2102) with the MUF standard in Drinking water. The signal decreased consistent with the MUF concentration decreasing from 10 μM (2103), 5 μM (2104), 2.5 μM (2105), and 1.25 μM (2106), and no signal was seen from the control (2107). The FIG. 22 graph is the RFU (2201) over time (2202) with the MUF standard in seawater. The signal decreased consistent with the MUF concentration decreasing from 5 μM (2203), 2.5 μM (2204), and 1.25 μM (2205), and no signal from the control (2206). The seawater showed higher fluorescence signals than the drinking water for the same concentration of MUF standard.

Figure 23:
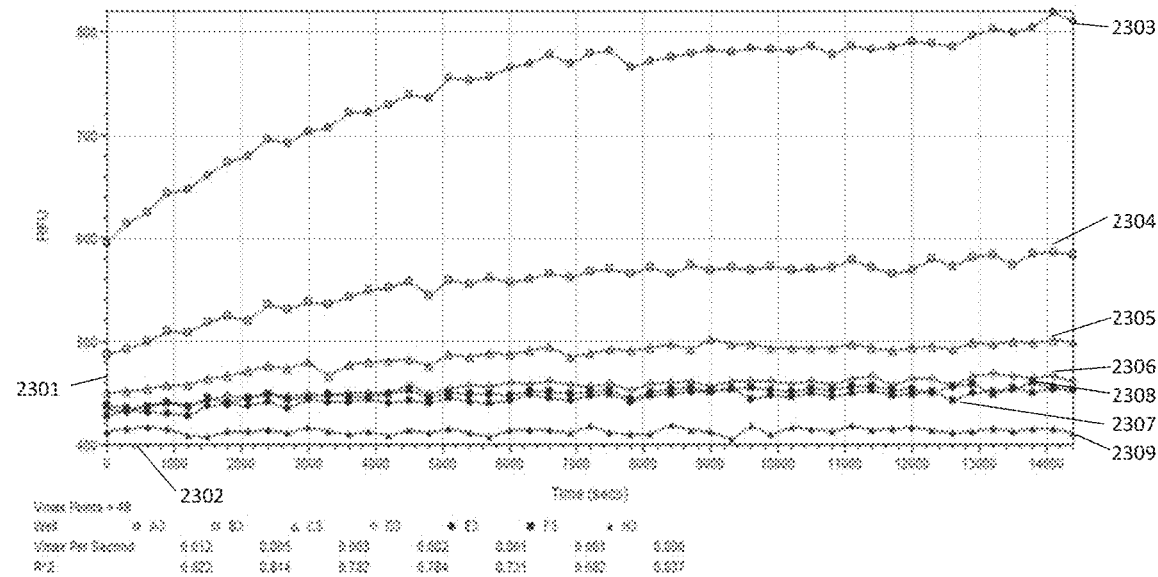
FIG. 23 is a graph of MUF-hepatonate titrated (0-80 µM) in a standardized drinking water inoculum.
Figure 24:
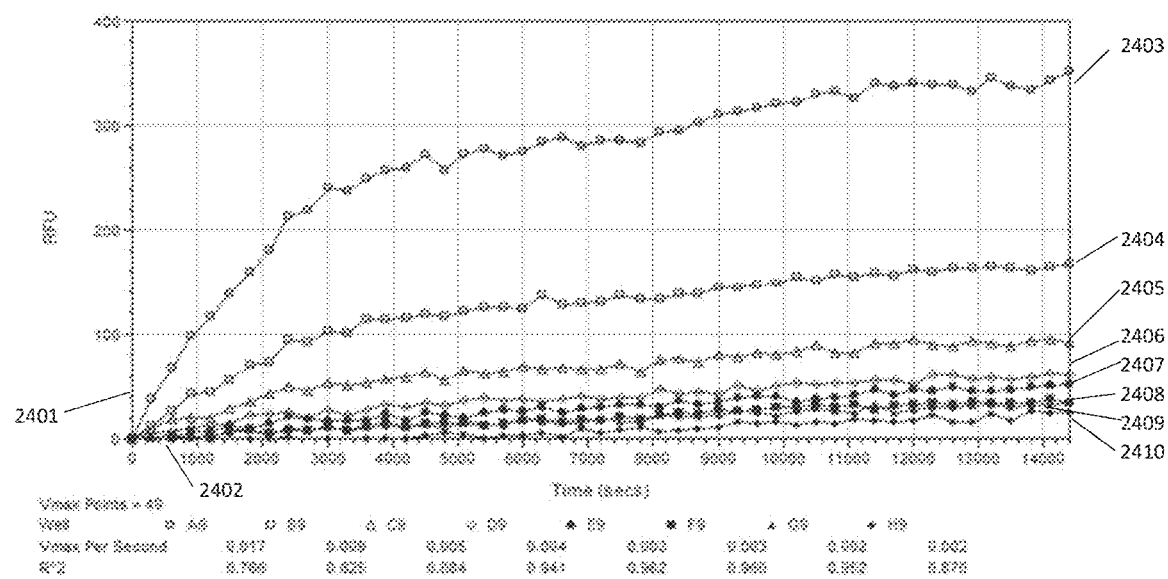
FIG. 24 is a graph of MUF-hepatonate titrated (0-80 µM) in a standardized seawater inoculum.

MUF-heptanoate—The FIG. 23 graph is the RFU (2301) over time (2302) with MUF-heptanoate in Drinking water. The signal decreased consistent with the MUF-heptanoate concentration decreasing from 80 μM (2303), 40 μM (2304), 20 μM (2305), 10 μM (2306), 5 μM (2307), and 2.5 μM (2308), and no signal was seen from the control (2309). The FIG. 24 graph is the RFU (2401) over time (2402) with MUF-heptanoate in seawater. The signal decreased consistent with the MUF concentration decreasing from 80 μM (2303), 40 μM (2304), 20 μM (2305), 10 μM (2306), 5 μM (2307), 2.5 μM (2308), and 1.25 μM (2409), with no signal from the control (2410). The drinking water showed higher fluorescence signals than the seawater for the same concentration of MUF-heptanoate.

Figure 25:
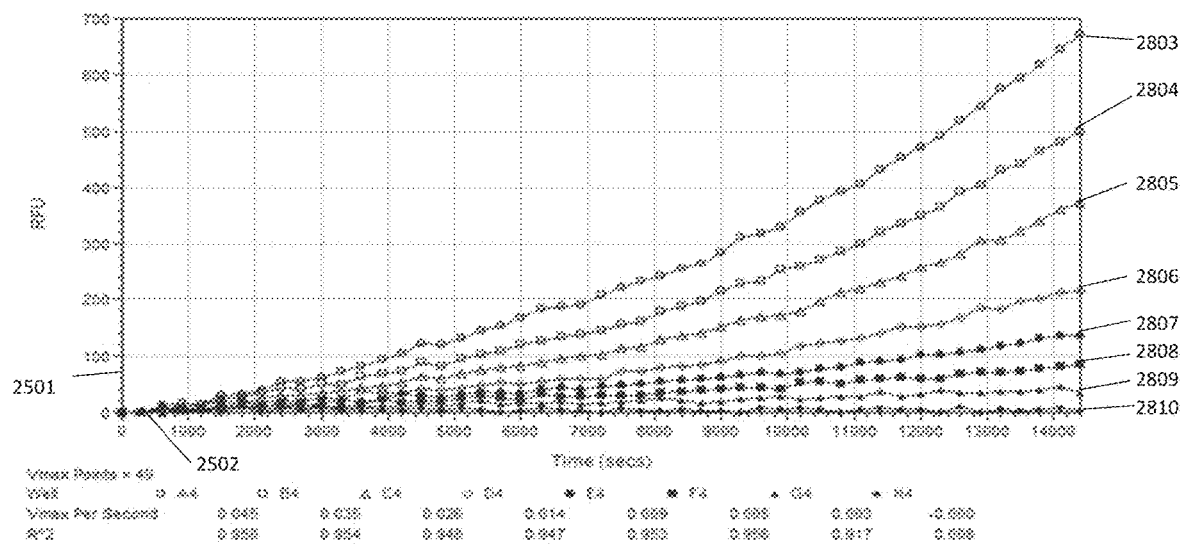
FIG. 25 is a graph of MUF-β-D-glucopyranoside titrated (0-40 µM) in a standardized drinking water inoculum.
Figure 26:
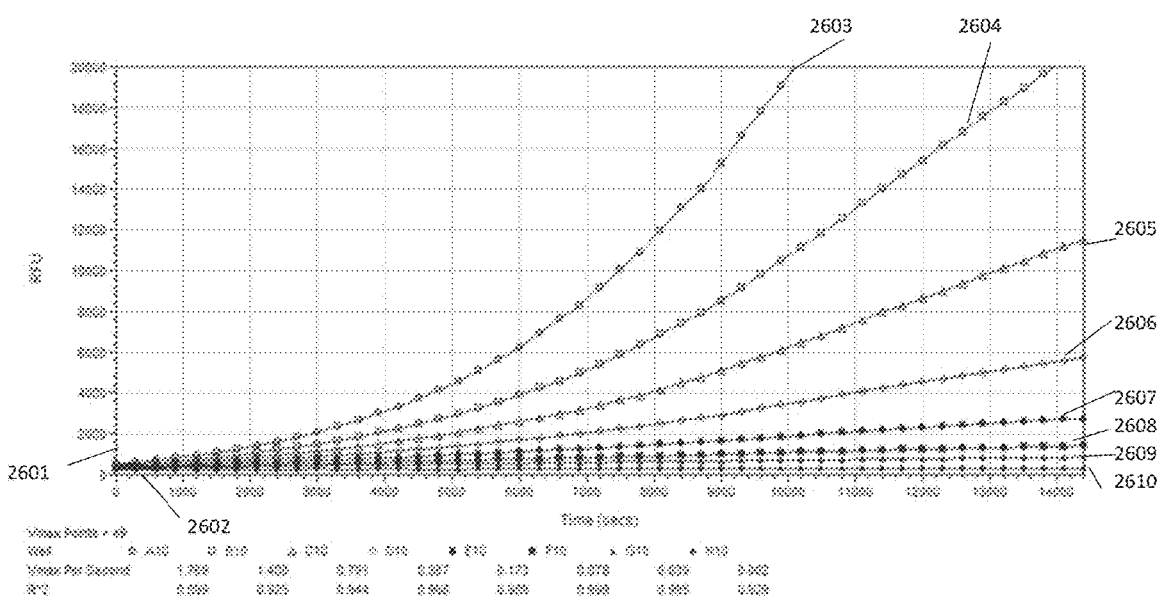
FIG. 26 is a graph of MUF-β-D-glucopyranoside titrated (0-40 µM) in a standardized seawater inoculum.

MUF-β-D-glucopyranoside—The FIG. 25 graph is the RFU (2501) over time (2502) with MUF-β-D-glucopyranoside in Drinking water. The signal decreased consistent with the MUF-β-D-glucopyranoside concentration decreasing from 40 μM (2503), 20 μM (2504), 10 μM (2505), 5 μM (2506), 2.5 μM (2507), 1.25 μM (2508), and 0.7 μM (2509), and no signal was seen from the control (2510). The FIG. 26 graph is the RFU (2601) over time (2602) with the MUF-β-D-glucopyranoside in seawater. The signal decreased consistent with the MUF concentration decreasing from 40 μM (2603), 20 μM (2604), 10 μM (2605), 5 μM (2606), 2.5 μM (2607), 1.25 μM (2608), and 0.7 μM (2609), and no signal was seen from the control (2610). The seawater showed higher fluorescence signals than the drinking water for the same concentration of MUF-β-D-glucopyranoside.

Figure 27:
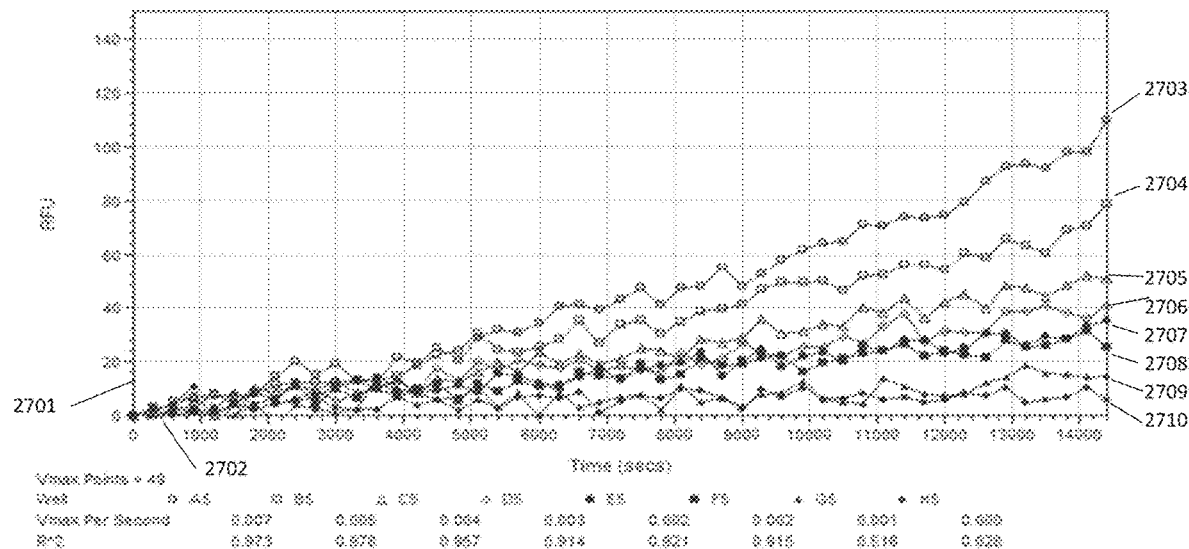
FIG. 27 is a graph of MUF-N-acetyl-β-D-glucosaminide titrated (0-80 µM) in a standardized drinking water inoculum.
Figure 28:
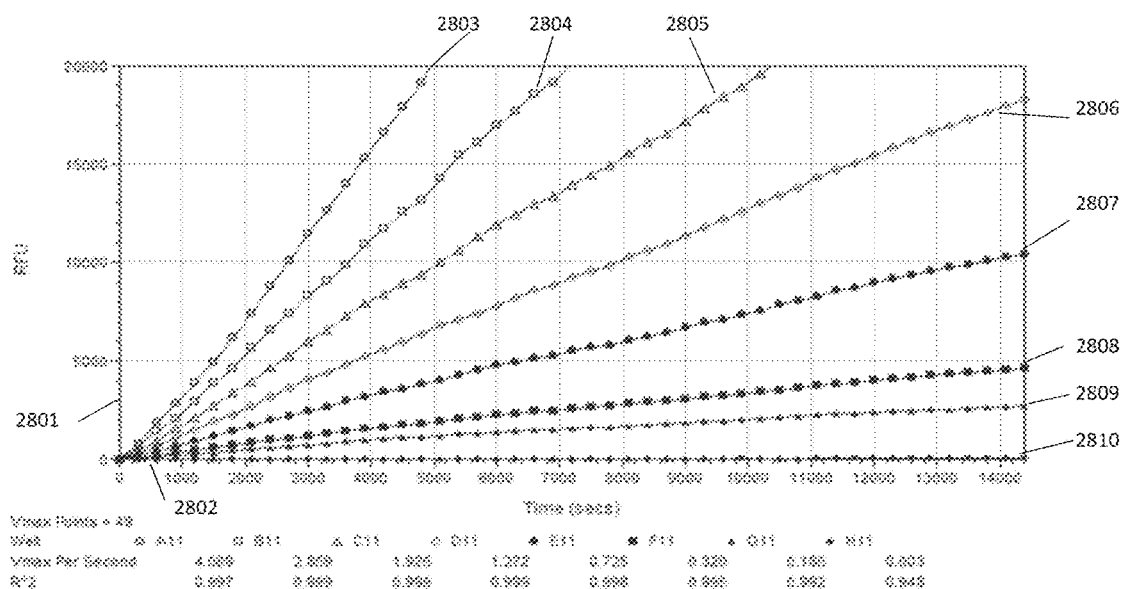
FIG. 28 is a graph of MUF-N-acetyl-β-D-glucosaminide titrated (0-80 µM) in a standardized seawater inoculum.

MUF-N-acetyl-β-D-glucosaminide—The FIG. 27 graph is the RFU (2701) over time (2702) with MUF-N-acetyl-β-D-glucosaminide in Drinking water. The signal decreased consistent with the MUF-N-acetyl-β-D-glucosaminide concentration decreasing from 80 μM (2703), 40 μM (2704), 20 μM (2705), 10 μM (2706), 5 μM (2707), 2.5 μM (2708), and 1.25 μM (2709), and no signal was seen from the control (2710). The FIG. 28 graph is the RFU (2801) over time (2802) with the MUF-N-acetyl-β-D-glucosaminide in seawater. The signal decreased consistent with the MUF concentration decreasing from 80 μM (2803), 40 μM (2804), 20 μM (2805), 10 μM (2806), 5 μM (2807), 2.5 μM (2808), and 1.25 μM (2809), and no signal was seen from the control (2810). The drinking water showed considerably less fluorescence than the seawater for the same concentration of MUF-N-acetyl-β-D-glucosaminide.

Figure 29:
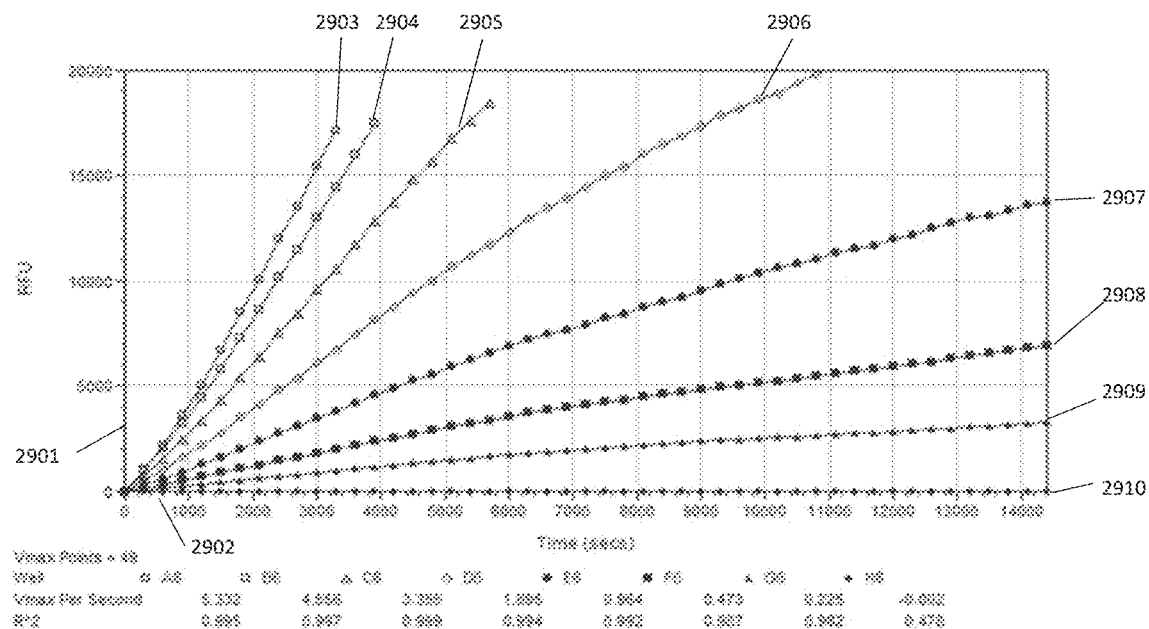
FIG. 29 is a graph of MUF-phosphate titrated (0-200 µM) in a standardized drinking water inoculum.
Figure 30:
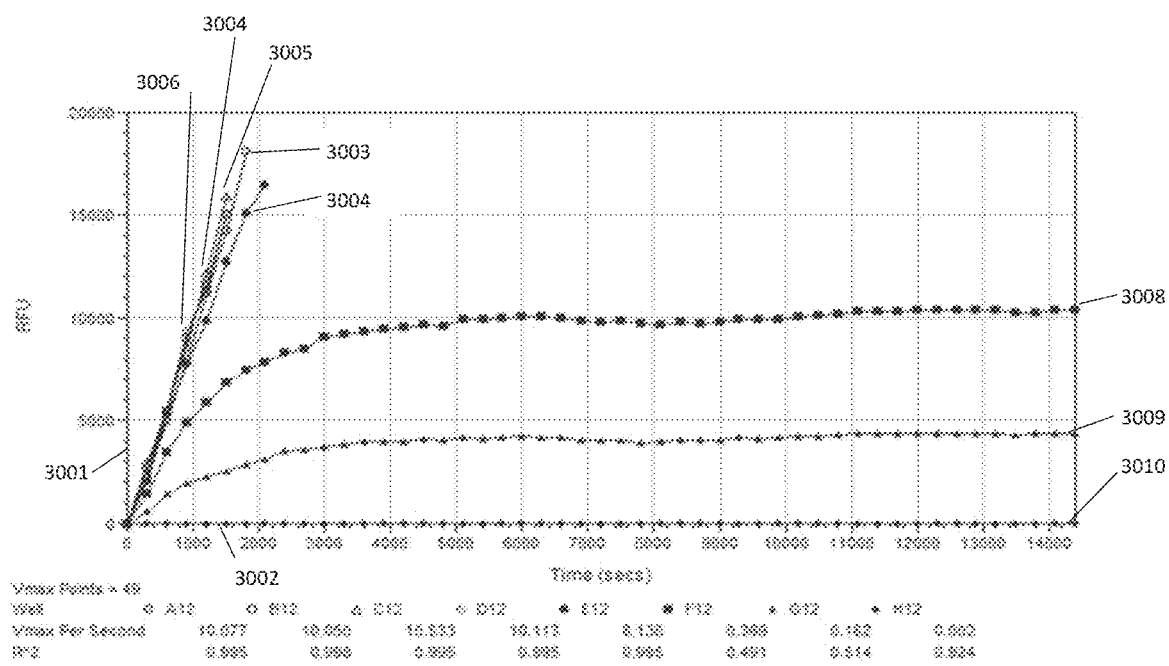
FIG. 30 is a graph of MUF-phosphate titrated (0-200 µM) in a standardized seawater inoculum.

MUF-phosphate—The FIG. 29 graph is the RFU (2901) over time (2902) with MUF-phosphate in Drinking water. The signal decreased consistent with the MUF-phosphate concentration decreasing from 200 μM (2903), 100 μM (2904), 50 μM (2905), 25 μM (2906), 12.5 μM (2907), 6 μM (2908), and 3 μM (2909), and no signal was seen from the control (2910). The FIG. 30 graph is the RFU (3001) over time (3002) with the MUF-phosphate in seawater. The signal decreased consistent with the MUF concentration decreasing from 200 μM (3003), 100 μM (3004), 50 μM (3005), 25 μM (3006), 12.5 μM (3007), 6 μM (3008), and 3 μM (3009), and no signal was seen from the control (3010). The higher concentrations (12.5-200 μM) of the MUF-phosphate in seawater had signals that were very close together. The fluorescence for MUF-phosphate was closer in range than for some of the other MUF-substrates.

Effect of final solution pH on EEA using the MUF fluorogenic substrates in seawater—Final solution pH is an important factor that affects both fluorogen fluorescence signal and reaction velocities in extracellular enzyme activity. Methylumbelliferone (MUF) fluorescence signal intensity increase as the final solution pH increases, in agreement with previously reported literature.

To assay the effect of pH on fluorogen-substrates, 40 mL of standardized Seawater inoculum was aliquoted into four 50 mL tubes with final pH adjusted as needed to pH 7-pH 10. For pH 8-pH 10, 0.1 M NaOH was added until the final solution was at the appropriate pH. Each pH solution was then further aliquoted into wells of a 96-well plate for fluorescence measurements using titrations of MUF standard, MUF-phosphate, or MUF-N-acetyl-τ3-D-glucosaminide.

Figure 31:
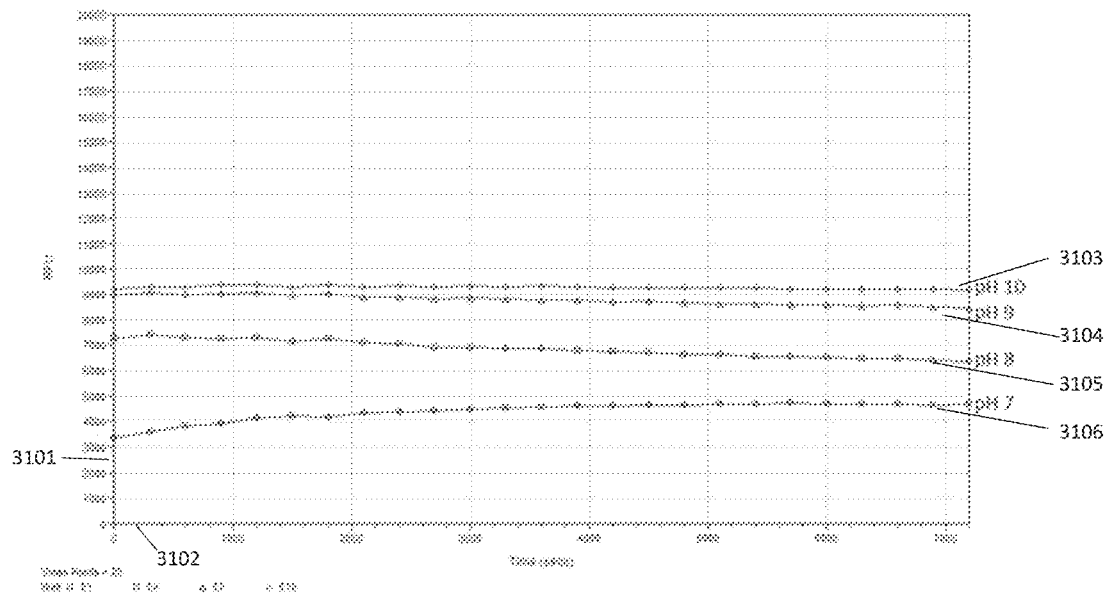
FIG. 31 is a graph of the effect of pH on 1.25 µM of MUF Standard (M1508) in seawater.

FIG. 31 is a graph of fluorescence signals in RFU (3101) over the testing time (3102) for a 1.25 μM MUF standard at various pH levels for the final solution. Fluorescence of the MUF standard increased (3106, 3105, 3104, 3103) as pH increased from pH 7-pH 10 and remained relatively constant over the testing time.

Figure 32:
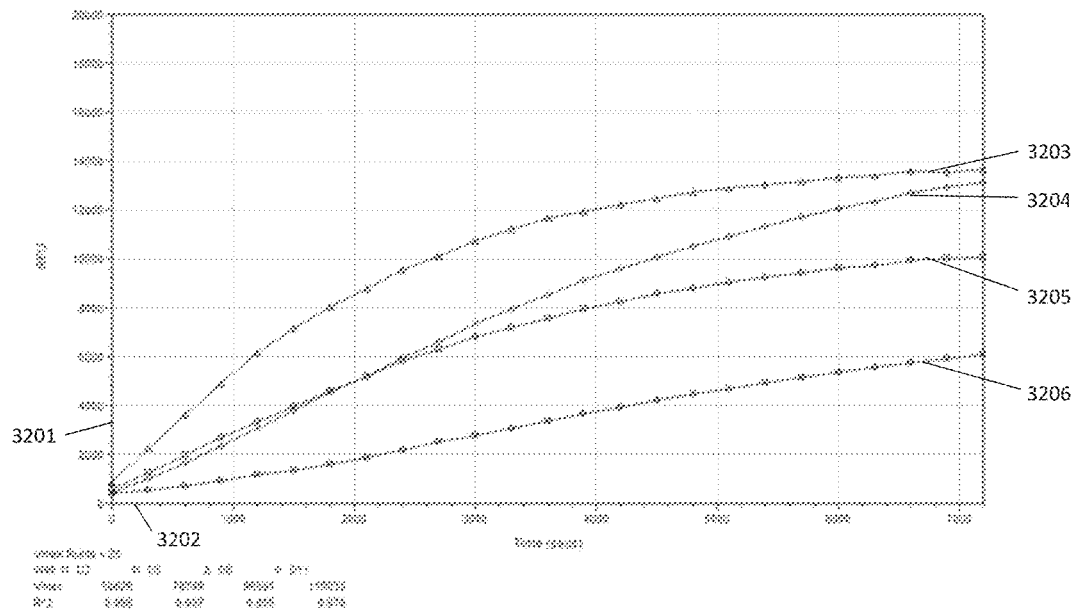
FIG. 32 is a graph of the effect of final solution pH on MUF-phosphate.

FIG. 32 is a graph of fluorescence signals in RFU (3201) over the testing time (3202) for MUF-phosphate at various pH levels for the final solution. Fluorescence of the MUF-phosphate increased (3206, 3205, 3203) as pH increased from 7-9, however at pH 10 (3204), the fluorescence signal was slightly lower than the signals at pH9.

Figure 33:
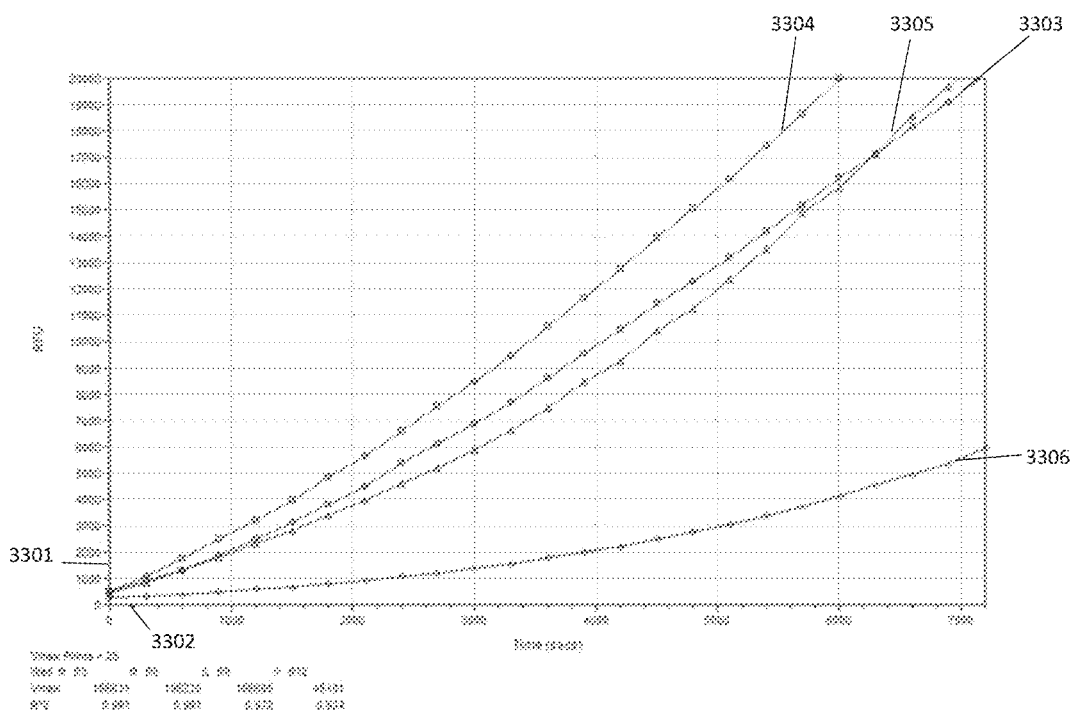
FIG. 33 is a graph of the effect of final solution pH on MUF-N-acetyl-β-D-glucosaminide.

FIG. 33 is a graph of fluorescence signals in RFU (3301) over the testing time (3302) for MUF-N-acetyl-β-D-glucosaminide at various pH levels for the final solution. Fluorescence of the MUF-N-acetyl-β-D-glucosaminide was fairly close over the range from pH 7-pH 9 (3303, 3304, 3305), but a substantial decrease was seen when the solution was at pH 10 (3306).

Enzymes have pH optimums that vary depending on the characteristics of the active site. pH affects the ionization of these sites, thereby increasing or decreasing catalytic potential. Extreme pH can also denature enzymes, retarding activity, and as seen in FIGS. 13 and 14, pH also has an effect of on reaction velocity as measured for MUF-phosphate and MUF-n-a-β-D-glucosaminide.

These results demonstrate that pH has an effect on both fluorogen intensity and the rate of enzyme activity leading to fluorogenic product production. Optimum pH levels have been demonstrated for particular fluorogens and substrates, which are parabolic in nature and these parameters must be considered when selecting the EEA assay conditions.

Heat profiling of EEA and F-S—Fluorogen signal intensity and extracellular enzyme activity were measured at temperatures from 25° C. to 55° C. to profile the effect of temperature on the activity.

Figure 34:
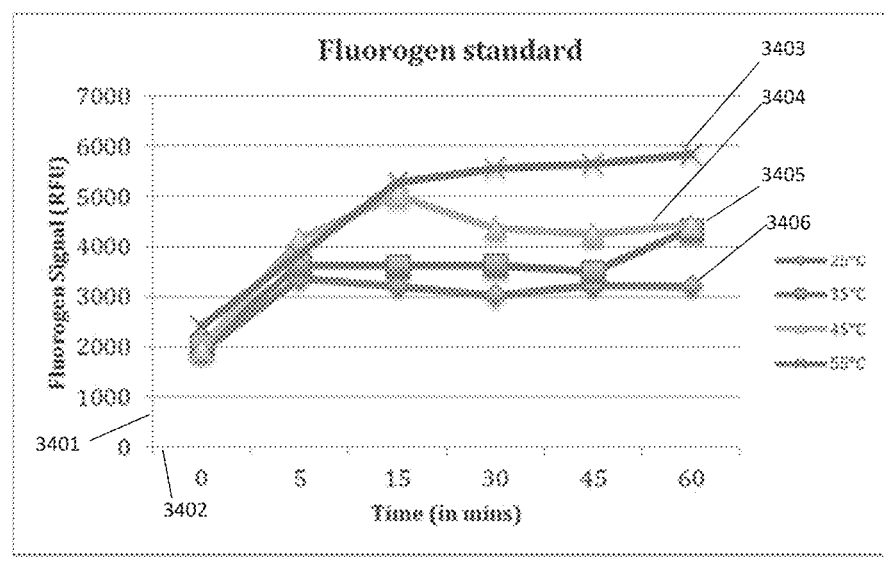
FIG. 34 is a graph of a temperature profile for MUF fluorogen standard.

The FIG. 34 graph shows the effect of temperature on MUF fluorogen standard fluorescence signal intensity (3401) over time (3402). The signal intensity increases (3406, 3405, 3404, and 3403) as temperature increases from 25° C. to 55° C.

Figure 35:
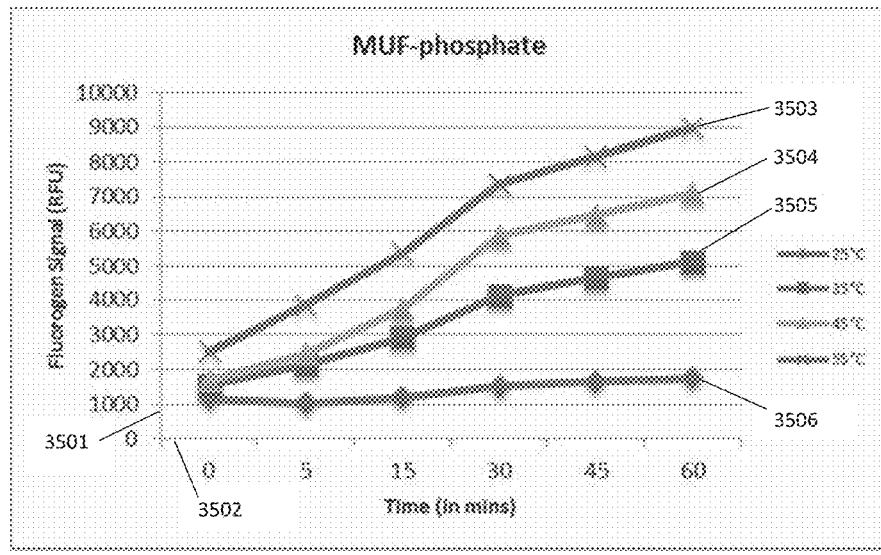
FIG. 35 is a graph of a temperature profile for MUF-phosphate activity.

The FIG. 35 graph shows the effect of temperature on MUF-phosphate fluorescence signal intensity (3501) over time (3502). The signal intensity increases (3506, 3505, 3504, and 3503) as temperature increases from 25° C. to 55° C.

Figure 36:
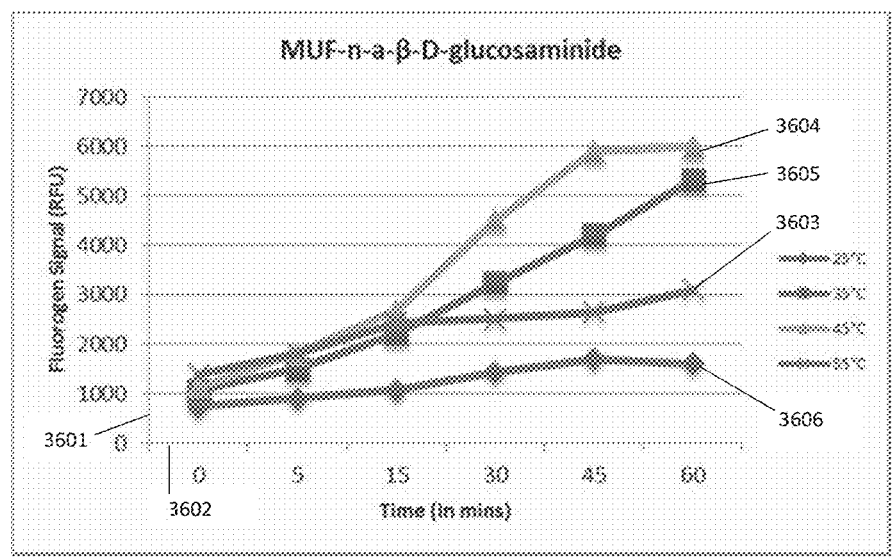
FIG. 36 is a graph of a temperature profile of MUF-N-acetyl-B-D-glucosaminide activity.

The FIG. 36 graph shows the effect of temperature on MUF-N-acetyl-β-D-glucosaminide fluorescence signal intensity (3601) over time (3602). The signal intensity increases (3606, 3605, and 3604) as temperature increases from 25° C. to 45° C.; however the signal has a significant decrease in intensity at 55° C.

The fluorogen-substrates tested have different fluorescence profiles for the temperature ranges tested and temperature must be considered when selecting the EEA assay conditions.

Figures 37A, 37B:
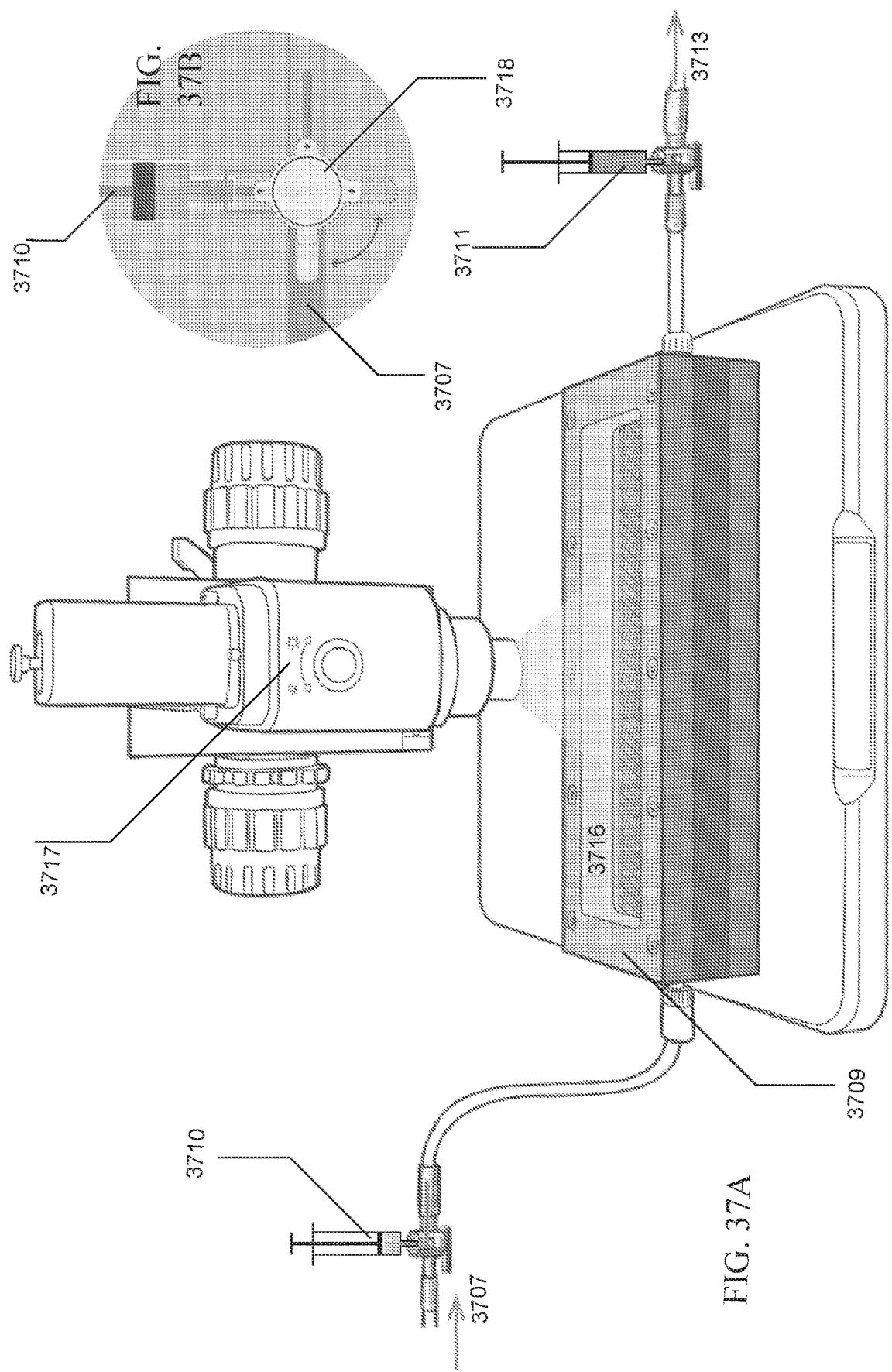
FIG. 37A is a schematic of an at-line filtration system showing ports and an optional integrated video camera.
FIG. 37B is an enlarged view of the injection port in FIG. 37A.

FIG. 37A is a schematic of an at-line filtration system along the lines of the system in FIGS. 6A and 6B, showing examples of an injection port (3710) along an inlet conduit (3707) proximal to the at-line sensor (3709), and a sample (flush) port (3711) along an outlet conduit (3713) distal to the al-line sensor (3709). When the valves (not shown) along the main feed solution stream are open, a portion of the feed solution stream is directed from the main feed solution stream via the inlet conduit (3707) to the at-line sensor (3709). The injection port (3710) positioned along the inlet conduit (3707) allows for introduction of fluorogen to the feed solution. The sample (flush) port (3711) positioned along the outlet conduit (3713) allows for removal of samples for fluorescence testing.

As seen in the FIG. 37B enlargement, the inlet port (3710) has a three-way valve (3718) that allows for feed solution to be directed to one of three paths. In the first (open) position, the feed solution flows unobstructed the through inlet conduit (3707) to the at-line sensor (3709), and in the second (closed) position, feed solution is prevented from flowing through the injection port valve (3718) to the at-line sensor (3709). The third (open) position allows feed solution to flow out of the valve and be collected external to the filtration system. The sample (flush) port (3711) also has a three-way valve like the valve (3718) in the injection port (3710). The sample (flush) port three-way valve allows for flow through the outlet conduit (3713) when in the first (open) position, retains the feed solution in the conduit proximal to the sample (flush) port three-way valve when in the second (closed) position, and allows for feed solution to be flushed from the line and collected external to the filtration system when in the third (open) position.

During normal filtration use, the sensor inlet valve from the main feed solution stream (valve 606, as seen in FIG. 6B) and the injection port valve (3718) are open and the feed solution stream flows along the inlet conduit (3707) and through the at-line sensor (3709). The sensor outlet valve (valve 608, as seen in FIG. 6B), where the feed stream solution re-enters the main feed solution stream, and the sample (flush) port valve, are open and the feed solution stream flowing through the sensor (3709) continues along the feed stream outlet conduit (3713) passing back to the main feed solution stream, thus allowing the at-line sensor membrane to encounter the same water conditions as the main filtration system.

The inlet and outlet valves of the at-line sensor (3709) can be closed at set time points for gauging bacterial EEA without interrupting operation of the main membrane unit. Once the valves are closed, the selected Fluorogen-Substrate can be injected into the feed solution stream of the at-line sensor (3709) through the injection port (3710), while closing the injection port and sample port valves to retain the fluorogen substrate and allow for the allotted incubation time. Following incubation, aliquots are removed via the sampling port (3711) and read externally by a fluorometer in 96 well plate.

After testing, which typically lasts no more than 30 minutes, the sensor (3709) is flushed of residual F-S and byproducts by opening the valve in the sample (flush) port (3711) to the third (open) position to remove the Fluorogen-Substrate from the system. Flushing can be accomplished by injecting water at the injection port and removing it at the sample (flush) port valve, by opening the inlet valve and allowing the feed solution to drain through the open (third position) sample (flush) port valve, or by other means sufficient to flush the Fluorogen-Substrate from the system prior to reestablishing unobstructed flow of the feed solution stream. After flushing is completed, the valves are all reopened and the feed stream again passes through the sensor (3709) and flows via conduit (3713) to the main feed solution stream as before. At each time point, 30 minutes of fluorogen-substrate incubation was selected as a balance between realistic sampling time and resulting signal strength; however the dwell time of the Fluorogen-Substrate in the sensor can range from 1 minute to 60 minutes as needed for the testing parameters. Increasing the incubation time should result in increased signal strength as more fluorogen liberation can occur.

Alternatively, liberated fluorogens from the EEA assay can be detected using an online fluorometer. For online fluorescence testing, an optional video camera with an integrated probe (3717) is positioned adjacent to an at-line sensor (3709) having an optional viewing pane (3716), as seen in FIG. 37A. At the set time points for gauging bacterial EEA, valves are placed in the closed position, fluorogen is injected into the injection port (3710), and incubation proceeds as described above. After the allotted incubation time, the video camera with integrated probe (3717) is actuated to detect fluorescence at the viewing pane (3717) without interrupting operation of the main membrane unit. After testing, which typically lasts no more than 30 minutes, the sensor (3709) is flushed of residual F-S as described above to remove the fluorogen from the system. After flushing is completed, the valves are all reopened and the feed stream again passes through the sensor (3709) and flows via conduit (3713) to the main feed solution stream as before.

What is claimed is:

1. A method for detecting membrane fouling comprising the steps of:
   providing a membrane fouling sensor positioned adjacent to a feed solution stream in a membrane filtration system, wherein a portion of a feed solution stream flows through the membrane fouling sensor contacting a sensor membrane therein; said membrane fouling sensor having an inlet valve directing the feed stream to the sensor membrane and an outlet valve directing the feed stream from the sensor membrane back to the feed solution stream proximal to a main membrane filtration unit;
   allowing the feed solution stream to contact the membrane fouling sensor during the normal operation of the membrane filtration system, such that the sensor membrane is subject to substantially the same conditions as the membrane in the main membrane filtration unit;
   operating the membrane filtration system for a time period ranging from 1 hour to 100 hours, during which time the sensor membrane and the membrane in the main membrane filtration unit are exposed to any microorganisms in the feed solution stream and said microorganisms may adhere to the sensor membrane and the membrane in the main membrane filtration unit causing one or more biofilm to develop on the membranes and producing extracellular enzymes;
   creating a closed system in the membrane fouling sensor by closing the inlet and outlet valves thereby trapping a portion of the feed solution stream and any microbial extracellular enzymes in the membrane fouling sensor;
   injecting a fluorogen-substrate into the membrane fouling sensor via an inject port positioned distal to the inlet valve and proximal to the sensor membrane;
   allowing the fluorogen-substrate to contact the feed solution stream and any microbial extracellular enzymes trapped in the membrane fouling sensor for 1-60 minutes;
   removing a portion of the feed solution stream trapped in the membrane fouling sensor via the flush port;
   using a fluorometer to measure the removed portion of the feed solution stream for fluorescence produced from the fluorogen-substrate interaction with extracellular enzymes;
   correlating the measured fluorescence with extracellular enzyme activity in the sample; and
   using the correlation to determine a biofouling level of the membranes.

2. The method of claim 1, wherein the sensor membrane in the membrane fouling sensor is comparable to the membrane in the main membrane filtration unit such that the sensor membrane in the membrane fouling sensor experiences substantially the same conditions as the membrane in the main membrane filtration unit.

3. The method of claim 1, further comprising the step of flushing the closed membrane fouling sensor of fluorogen-substrate by injecting a cleaning solution via the inject port and removing the cleaning solution via the flush port.

4. The method of claim 1, further comprising the step of opening the inlet and outlet valves to allow feed stream solution to flow through the membrane fouling sensor.

5. The method of claim 1, wherein the membrane filtration system is used for desalination of the feed stream sample.

6. The method of claim 1 wherein the fluorogen-substrate comprises Methylumbelliferone (MUF).

7. The method of claim 6, wherein the MUF fluorogenic substrate is selected from MUF-phosphate, MUF-N-acetyl-β-D-glucosaminide, MUF-heptanoate and MUF-β-D-glucopyranoside.

8. A membrane fouling sensor comprising:
   a sensor unit positioned adjacent to a main feed solution stream proximal to a main membrane filtration unit in a membrane filtration system, said sensor unit having a filtration membrane;
   an inlet valve positioned at the main feed solution stream that diverts a portion of the main feed solution stream to the sensor unit as a sensor feed stream when opened and prevents the main feed solution stream from entering the sensor unit when closed;
   an outlet valve that directs the sensor feed stream back to the main feed solution stream, distal to the inlet valve and proximal to the main membrane filtration unit when opened, and retains the sensor feed stream in the sensor unit when closed,
   a feed stream conduit positioned between the inlet valve and the outlet valve that directs the main feed solution stream from the inlet valve to the outlet valve through the sensor unit,
   an inject port in the feed stream conduit distal to the inlet valve and proximal to the sensor unit; and
   a flush port in the feed stream conduit distal to the sensor unit and proximal to the outlet valve.

9. The membrane fouling sensor of claim 8, wherein the inlet valve and the outlet valve can be closed trapping the sensor feed stream in the conduit and sensor unit.

10. The membrane fouling sensor of claim 8, wherein one or more solution can be injected into the membrane fouling sensor via the inject port.

11. The membrane fouling sensor of claim 10, wherein the one or more solution is a fluorogenic-substrate that can be cleaved by one or more extracellular enzymes in the sensor feed stream.

12. The membrane fouling sensor of claim 8, wherein a portion of the sensor feed stream can be removed via the flush port.

13. The membrane fouling sensor of claim 8, wherein the feed stream conduit and sensor unit can be flushed of materials by injecting a solution in through the inject port and removing the solution through the flush port.

14. The membrane fouling sensor of claim 8, wherein the filtration membrane in the sensor unit is comparable to the membrane in the main membrane filtration unit such that the filtration membrane in the sensor unit experiences substantially the same conditions as the membrane in the main membrane filtration unit.

15. The membrane fouling sensor of claim 8, wherein the membrane in the main membrane filtration unit is selected from membranes for microfiltration, ultrafiltration, nanofiltration, reverse osmosis or forward osmosis.

16. A method of detecting biofouling of a membrane comprising the steps of:
    collecting a sample of a permeate from a membrane filtration system, said permeate resulting when a feed stream solution has been filtered by the membrane;
    selecting a fluorogen-substrate comprising Methylumbelliferone (MUF) that can be cleaved by one or more microbial extracellular enzymes;
    mixing the permeate sample with the fluorogen-substrate;
    using a fluorometer to measure fluorescence produced by the interaction of one or more microbial extracellular enzymes in the permeate sample on the fluorogen-substrate;
    correlating the fluorescence of the permeate sample and fluorogen-substrate mixture to determine the level of extracellular enzyme activity in the permeate as an indication of biofouling of the membrane; and
    adjusting a pH of the fluorogen-substrate to a range of pH7-pH10 prior to mixing with the permeate sample.

17. The method of claim 16, further comprising adjusting a temperature of the fluorogen-substrate and permeate sample to a range from 25°-55° C. prior to measuring fluorescence.

18. The method of claim 16, wherein the membrane filtration system is used for desalination of the feed stream solution.

19. The method of claim 16, wherein the fluorogenic substrate comprising Methylumbelliferone (MUF) is selected from MUF-phosphate, MUF-N-acetyl-β-D-glucosaminide, MUF-heptanoate and MUF-β-D-glucopyranoside.

* * * * *